(12) United States Patent
Kretzer et al.

(10) Patent No.: US 8,968,367 B2
(45) Date of Patent: Mar. 3, 2015

(54) COMPRESSION-DISTRACTION SPINAL FIXATION SYSTEM AND KIT

(75) Inventors: Ryan M. Kretzer, Baltimore, MD (US); Bryan W. Cunningham, Baltimore, MD (US); Jeffrey Gordon, Saratoga Springs, NY (US)

(73) Assignees: The Johns Hopkins University, Baltimore, MD (US); Neuraxis Technologies LLC, Baltimore, MD (US)

( * ) Notice: Subject to any disclaimer, the term of this patent is extended or adjusted under 35 U.S.C. 154(b) by 13 days.

(21) Appl. No.: 13/176,594

(22) Filed: Jul. 5, 2011

(65) Prior Publication Data

US 2011/0319939 A1    Dec. 29, 2011

Related U.S. Application Data

(63) Continuation-in-part of application No. 12/958,304, filed on Dec. 1, 2010, now Pat. No. 8,864,800.

(60) Provisional application No. 61/292,215, filed on Jan. 5, 2010, provisional application No. 61/383,540, filed on Sep. 16, 2010, provisional application No. 61/490,851, filed on May 27, 2011.

(51) Int. Cl.
*A61B 17/70* (2006.01)
*A61B 17/86* (2006.01)

(52) U.S. Cl.
CPC .......... *A61B 17/7032* (2013.01); *A61B 17/7002* (2013.01); *A61B 17/7037* (2013.01); *A61B 17/7079* (2013.01); *A61B 17/7014* (2013.01)
USPC ........... 606/264; 606/86 A; 606/305; 606/105

(58) Field of Classification Search
CPC ........ A61B 17/7046; A61B 17/7016–17/7017; A61B 17/7014; A61B 17/7077; A61B 17/7079; A61B 17/708
USPC ....... 606/246–279, 104–105, 86 A, 305, 308, 606/53–60
See application file for complete search history.

(56) References Cited

U.S. PATENT DOCUMENTS

| | | | |
|---|---|---|---|
| 4,085,744 A * | 4/1978 | Lewis et al. | 623/17.11 |
| 4,567,884 A * | 2/1986 | Edwards | 606/330 |
| 4,771,767 A | 9/1988 | Steffee | |
| 4,854,304 A | 8/1989 | Zielke | |
| 4,896,661 A * | 1/1990 | Bogert et al. | 606/86 R |

(Continued)

OTHER PUBLICATIONS

International Search Report issued in Application No. PCT/US2012/039848 dated Nov. 23, 2012.

*Primary Examiner* — Ellen C Hammond
*Assistant Examiner* — Jacqueline Johanas
(74) *Attorney, Agent, or Firm* — Venable LLP; Henry J. Daley; Tamatane J. Aga

(57) ABSTRACT

Compression-distraction spinal fixation systems, and methods of performing compression-distraction spinal fixation, are provided that include screw-rod constructs having a ratcheting mechanism. Bone screws of the screw-rod constructs can have a pawl that engages ratchet teeth on the rod of the screw-rod construct. The bone screw can be unidirectionally ratcheted along the length of the rod to apply compressive or distractive forces. Tools for manipulation of the screw-rod constructs are also provided, which tools include distal tips configured to engage the bone screws.

16 Claims, 20 Drawing Sheets

(56) References Cited

U.S. PATENT DOCUMENTS

| | | | | |
|---|---|---|---|---|
| 5,167,662 A * | 12/1992 | Hayes et al. | | 606/916 |
| 5,330,473 A | 7/1994 | Howland | | |
| 5,672,177 A * | 9/1997 | Seldin | | 606/71 |
| 5,700,263 A * | 12/1997 | Schendel | | 606/57 |
| 5,702,395 A * | 12/1997 | Hopf | | 606/250 |
| 5,716,356 A * | 2/1998 | Biedermann et al. | | 606/271 |
| 5,928,231 A * | 7/1999 | Klein et al. | | 606/60 |
| 5,961,517 A * | 10/1999 | Biedermann et al. | | 606/86 A |
| 6,277,124 B1 * | 8/2001 | Haag | | 606/105 |
| 6,749,613 B1 * | 6/2004 | Conchy et al. | | 606/57 |
| 7,011,658 B2 | 3/2006 | Young | | 606/258 |
| 7,578,822 B2 | 8/2009 | Rezach et al. | | |
| 7,776,051 B2 * | 8/2010 | Colleran et al. | | 606/105 |
| 7,815,666 B2 * | 10/2010 | Baynham et al. | | 606/280 |
| 7,981,115 B2 * | 7/2011 | Justis et al. | | 606/102 |
| 8,021,396 B2 * | 9/2011 | Winslow et al. | | 606/264 |
| 8,048,129 B2 * | 11/2011 | Forton et al. | | 606/279 |
| 8,083,750 B2 * | 12/2011 | Lim et al. | | 606/105 |
| 8,088,149 B2 | 1/2012 | White | | |
| 8,142,483 B2 * | 3/2012 | Drewry et al. | | 606/279 |
| 8,177,810 B2 * | 5/2012 | Ferree | | 606/246 |
| 8,236,002 B2 | 8/2012 | Fortin et al. | | |
| 8,372,081 B1 * | 2/2013 | Schafer et al. | | 606/90 |
| 8,414,581 B2 * | 4/2013 | Shah et al. | | 606/54 |
| 8,439,914 B2 * | 5/2013 | Ross et al. | | 606/56 |
| 2002/0116001 A1 | 8/2002 | Schafer et al. | | |
| 2003/0055430 A1 * | 3/2003 | Kim | | 606/69 |
| 2004/0153067 A1 * | 8/2004 | Smith et al. | | 606/60 |
| 2005/0043730 A1 * | 2/2005 | Janowski et al. | | 606/56 |
| 2006/0064092 A1 | 3/2006 | Howland | | |
| 2006/0195088 A1 | 8/2006 | Sacher et al. | | |
| 2007/0093846 A1 * | 4/2007 | Frigg et al. | | 606/90 |
| 2007/0233086 A1 * | 10/2007 | Harms et al. | | 606/61 |
| 2007/0276371 A1 * | 11/2007 | Baynham et al. | | 606/61 |
| 2008/0177334 A1 | 7/2008 | Stinnette | | |
| 2009/0024165 A1 * | 1/2009 | Ferree | | 606/246 |
| 2009/0048631 A1 | 2/2009 | Bhatnagar et al. | | |
| 2009/0204150 A1 * | 8/2009 | Hochschuler et al. | | 606/246 |
| 2009/0216273 A1 | 8/2009 | Cox | | |
| 2009/0281542 A1 * | 11/2009 | Justis | | 606/60 |
| 2010/0030283 A1 * | 2/2010 | King et al. | | 606/86 A |
| 2010/0069972 A1 * | 3/2010 | Jones et al. | | 606/86 A |
| 2010/0145388 A1 | 6/2010 | Winslow et al. | | |
| 2010/0152734 A1 * | 6/2010 | Mulone | | 606/60 |
| 2010/0198261 A1 | 8/2010 | Trieu et al. | | |
| 2010/0241172 A1 | 9/2010 | Biyani et al. | | |
| 2010/0324600 A1 | 12/2010 | Biyani | | |
| 2010/0331849 A1 | 12/2010 | Riesinger et al. | | |
| 2011/0098757 A1 | 4/2011 | Schelling | | |
| 2011/0118784 A1 * | 5/2011 | Baynham et al. | | 606/264 |
| 2011/0184465 A1 * | 7/2011 | Boehm | | 606/264 |
| 2011/0224740 A1 * | 9/2011 | Smisson et al. | | 606/86 A |
| 2011/0251646 A1 | 10/2011 | Karnezis | | |
| 2012/0022597 A1 * | 1/2012 | Gephart et al. | | 606/279 |
| 2012/0116467 A1 * | 5/2012 | King et al. | | 606/86 A |
| 2012/0197301 A1 * | 8/2012 | Foley et al. | | 606/279 |
| 2012/0197318 A1 * | 8/2012 | Barry et al. | | 606/86 A |
| 2012/0215262 A1 * | 8/2012 | Culbert et al. | | 606/279 |
| 2012/0239092 A1 * | 9/2012 | Jones et al. | | 606/278 |
| 2013/0245692 A1 * | 9/2013 | Hayes et al. | | 606/279 |

* cited by examiner

COMPRESSION-DISTRACTION SPINAL FIXATION SYSTEM AND KIT

CROSS-REFERENCE TO RELATED APPLICATIONS

This application is a continuation-in-part of co-pending U.S. patent application Ser. No. 12/958,304, filed Dec. 1, 2010, which claims the priority benefit under 35 U.S.C. §119(e) of U.S. Provisional Application No. 61/292,215, filed on Jan. 5, 2010, and U.S. Provisional Application No. 61/383,540, filed on Sep. 16, 2010. This application also claims the priority benefit under 35 U.S.C. §119(e) of U.S. Provisional Application No. 61/490,851, filed on May 27, 2011. The entire disclosure of each of the foregoing applications is considered part of and is incorporated by reference in the disclosure of this application.

BACKGROUND

1. Field of Invention

The present technology relates to an implant for surgical treatment of the spine, and methods for stabilizing a spine using the implants. More particularly, the present technology provides compression-distraction spinal fixation systems that include screw-rod constructs.

2. Discussion of Related Art

Anterior, posterior and lateral spinal fixation is commonly used for the treatment of degenerative disease, trauma, deformity, and oncological processes. The current state of the art includes the placement of rigid bone screws into the posterior arch, pedicles or vertebral bodies of adjacent spinal segments. These bone screws are then connected to each other by rigid metal rods in order to stabilize the spine and enable progressive bony fusion. Such bone screw-rod constructs have gained prominence due to their superior biomechanical stability relative to alternate fixation techniques, such as wiring, etc., as well as the benefits provided by three column fixation of the spine. Such systems have been made more versatile in recent years with the advent of polyaxial screw head technology, which allows more complex construct placement and screw connections. While current screw-rod systems are ideal for fixating motion segments in the spine in neutral position, certain situations call for the application of compressive or distractive forces in order to improve spinal balance and to aid in spinal fusion.

Current screw based spinal fixation systems use smooth, cylindrical metal or ceramic rods to connect screws that are anchored in bony portions of each vertebral level, such as the pedicle, lateral mass, lamina, and/or vertebral body. One example of a currently known screw based spinal fixation system is illustrated in FIG. 1. As shown in FIG. 1, a bone screw 10 connected to a rod 12. Rod 12 is cylindrical, and has a smooth outer surface. Bone screw 10 has a screw head 14, which can have a variable angle head, as shown, or it could be a fixed angle screw. Bone screw 10 includes a threaded shaft 16 attached to the screw head 14. Bone screw 10 also includes a set screw 18 that is attached to the screw head 14. Bone screw 10 can be connected to the rod 12 by attaching the bone screw to the desired bony spinal portion, sliding the rod 12 onto the bone screw, and then tightening the set screw 18 to secure the bone screw 10 at a desired location on the rod 12.

After placing this instrumentation, spine surgeons typically apply compressive forces manually between adjacent screws in order to increase lordosis for improved sagittal balance, or to compress upon an interbody graft in order to improve fusion. Alternatively, surgeons may wish to apply distractive forces between adjacent screws in order to improve access to the disc space for discectomy or interbody graft placement, or to affect deformity correction. Due to the smooth, cylindrical rod design, current spinal fixation systems do not provide or allow for the maintenance of compressive or distractive forces. Instead, one surgeon must provide manual compression between two screws while a second surgeon attempts to tighten the rod in place at each fixation point. This technique is both cumbersome and technically challenging.

SUMMARY

The present technology relates to compression-distraction spinal fixation systems that include screw-rod constructs that include a ratcheting mechanism. Tools for manipulation of the screw-rod constructs are also provided.

According to an embodiment, a compression-distraction spinal fixation system is provided that includes at least one bone screw and a toothed rod. The bone screw can include a threaded shaft, a screw head, a set screw, and a pawl. The toothed rod can have a plurality of ratchet teeth that receive the pawl of the bone screw, whereby the bone screw is releasably coupled to and selectively moveable unidirectionally along the toothed rod.

According to another embodiment, a compression tool for use with a spinal fixation system is provided. The compression tool may include first and second handle portions pivotably coupled to one another about a common fulcrum, and first and second extension portions connected, respectively, to the first and second handle portions. The first and second extension portions may include distal tips configured to engage a portion of adjacent bone screws of the spinal fixation system to allow manual manipulation of the bone screws unidirectionally toward one another along a toothed rod of the spinal fixation system.

According to another embodiment, a distraction tool for use with a spinal fixation system is provided. The distraction tool may include first and second handle portions pivotably coupled to one another at a pivot point, and first and second extension portions connected, respectively, to the first and second handle portions. The first and second extension portions may include distal tips configured to engage a portion of adjacent bone screws of the spinal fixation system to allow manual manipulation of the bone screws unidirectionally away from one another along a toothed rod of the spinal fixation system.

According to another embodiment, a spinal fixation kit is provided. The kit may include a bone screw, a toothed rod, and a compression and/or distraction tool. The bone screw may include a pawl. The toothed rod has a plurality of ratchet teeth. The bone screw is configured to be releasably coupled to and selectively moveable along the toothed rod. The pawl of the bone screw is configured to engage the ratchet teeth of the toothed rod to allow unidirectional movement of the bone screw along the toothed rod. The compression tool may include distal tips configured to engage a portion of the bone screw and move the same unidirectionally along the toothed rod. The compression tool may include handle portions pivotably coupled to one another about a common fulcrum, and respective extension portions connected to the handle portions. The distractor tool may include distal tips configured to engage a portion of the bone screw and move the same unidirectionally along the toothed rod. The distraction tool may include handle portions pivotably coupled to one another at a pivot point, and respective extension portions connected to the handle portions.

Further features and advantages, as well as the structure and operation of various embodiments of the invention, are described in detail below with reference to the accompanying drawings.

BRIEF DESCRIPTION OF THE DRAWINGS

Specific examples have been chosen for purposes of illustration and description, and are shown in the accompanying drawings, forming a part of the specification.

FIG. 36b illustrates a bottom perspective view of the pawl of the screw-rod construct illustrated in FIGS. 36 and 36a.

DETAILED DESCRIPTION

Figure 1:
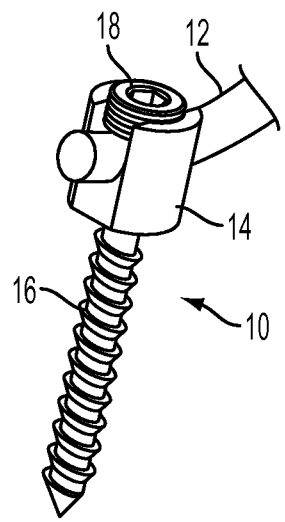
FIG. 1 illustrates one example of a prior art screw-rod construct.
Figure 2:
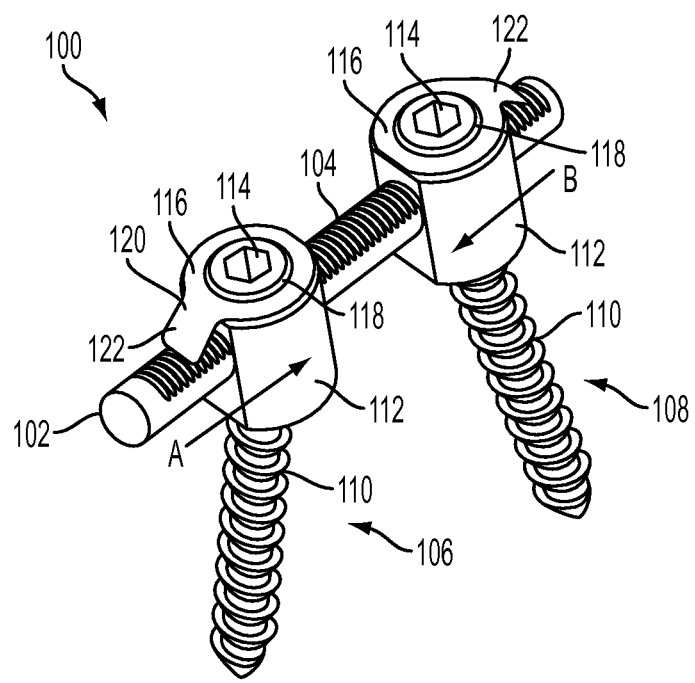
FIG. 2 illustrates one example of a screw-rod construct of the present technology.

The present technology relates to compression-distraction spinal fixation systems and kits that include screw-rod constructs and tools for manipulation of such screw-rod constructs. More particularly, the present technology provides a rod and screws that incorporate a ratchet and pawl mechanism for imposition of compression and distraction forces on the spinal column. Preferably, compression-distraction spinal fixation systems described herein can allow a single surgeon the ability to apply compressive or distractive forces as desired between adjacent spinal levels in a seamless and efficient manner. By employing the unique ratcheting mechanism provided in compression-distraction spinal fixation systems of the present technology, which in at least some examples can integrate into existing bone-screw rod technology, regional forces can be maintained segmentally or across the entirety of a given spinal construct, avoiding the cumbersome technique of compression/distraction that is inherent to traditional screw-rod systems. Combining improvements in maintenance of regional forces with ease of application and use, the compression-distraction spinal fixation systems of the present technology can add to a spine surgeon's armamentarium in the treatment of complex spinal disease.

Compression-distraction spinal fixation systems of the present technology are more particularly described in the following examples with reference to the accompanying drawings, and are intended as illustrative only. Referring to the drawings, like numbers indicate like parts throughout the views. Compression-distraction spinal fixation systems of the present technology include a toothed rod and at least one bone screw of the present technology. In some examples, compression-distraction spinal fixation systems of the present technology include a toothed rod, at least one bone screw of the present technology, and at least one conventional bone screw. In other examples, compression-distraction spinal fixation systems of the present technology include a toothed rod, a first bone screw of the present technology, and a second bone screw of the present technology.

As used in the description herein, and throughout the claims that follow, the meaning of "ratcheting the bone screw along the length of the toothed rod" means that the position of the bone screw is changed with respect to its original position along the length of the toothed rod due to movement of the bone screw, movement of the rod, or movement of both the bone screw and the rod. As used in the description herein, and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

The rods of compression-distraction spinal fixation systems of the present technology include ratchet teeth, which are preferably evenly spaced along a portion of the length of the rod, preferably along the entire length or substantially the entire length of the rod. Placing evenly spaced ratchet teeth along the length of the rod can allow the rod to be cut and contoured as desired in the operating room. In some examples, precut and precontoured rods can be provided, such as for example, for short segment constructs typically spanning 2, 3, and 4 vertebral levels. The ratchet teeth can cover at least a portion of the outer surface, or circumference, of the rod, including but not limited to, the entire circumference of the rod, half the circumference of the rod, one third of the circumference of the rod, one quarter of the circumference of the rod, or any other suitable portion of the circumference of the rod. The ratchet teeth can be formed as depressions in a toothed rod, or as protrusions that extend from the toothed rod. Toothed rods of the present technology can be made from any suitable material, including but not limited to a biocompatible metal, such as titanium, titanium alloy, stainless steel or cobalt chromium; a biocompatible polymer, such as PEEK; a composite material such as carbon fiber; or a biocompatible metal coated with another biocompatible metal or biocompatible polymer. In at least some examples, the inner diameter of the toothed rods, which is the diameter of the rod not including the height of the ratchet teeth, can be the same as the diameters that are currently used with known smooth rods, which can provide the same mechanical strength as currently known rods.

Bone screws of the present technology can also be made from any suitable material, including but not limited to a biocompatible metal, such as titanium, titanium alloy, stainless steel or cobalt chrome; a biocompatible polymer, such as PEEK; a composite material such as carbon fiber; or a combination of these. Bone screws of the present technology include a pawl that can engage the teeth on the toothed rod to provide a ratcheting mechanism. The pawl engages at least one ratchet tooth at a location on the toothed rod, and can allow unidirectional ratcheting of the bone screw on the rod to maintain either a compressive or distractive force as desired. In some examples, pawls are flexible, while in others they are rigid. Some of the examples described herein include reversible pawls, meaning that the pawl can be adjusted to allow ratcheting in either direction along the length of the toothed rod, depending on the orientation of the pawl. In other examples, however, pawls that are not reversible, and that provide ratcheting in only a single direction, are also provided. Bone screws of the present technology can also include a shaft, such as a threaded shaft, that can be used to attach the bone screw to a desired bony portion of the spine. Bone screws of the present technology can further include a screw head, and a set screw.

FIGS. 2 through 6 illustrate one example of a screw-rod construct 100 of the present technology that includes a toothed rod 102 having ratchet teeth 104, a first bone screw 106 of the present technology and a second bone screw 108 of the present technology. In an alternative example, either bone screw 106 or bone screw 108 could be replaced with a conventional bone screw, such as bone screw 10 illustrated in FIG. 1. In the illustrated example of FIG. 2, each bone screw includes a threaded shaft 110, a screw head 112, a set screw 114, and a pawl 116. The set screw 114 of each bone screw includes a retaining ring 118, which retains the pawl 116 on the set screw 114. The pawl 116 is preferably flexible, and includes a bend 120 and a blade 122.

When the toothed rod 102 is slidably connected to the first bone screw 106 and the second bone screw 108, the blade 122 of each pawl 116 of each bone screw 106, 108 engages at least one tooth of the ratchet teeth 104 on toothed rod 102. The first bone screw 106 can be ratcheted along the toothed rod 102 in the direction indicated by arrow A, but the engagement of the blade 122 of the first bone screw 106 with the ratchet teeth 104 of the toothed rod 102 can prevent movement of the first bone screw 106 in the opposite direction. Likewise, the second bone screw 108 can be ratcheted along the toothed rod 102 in the direction indicated by arrow B, but the engagement of the blade 122 of the second bone screw 108 with the ratchet teeth 104 of the toothed rod 102 can prevent movement of the second bone screw 108 in the opposite direction.

Figure 3:
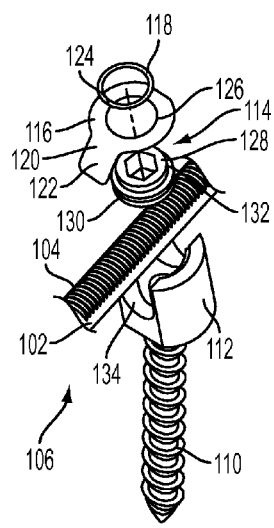
FIG. 3 illustrates an exploded view of the example of FIG. 2.

FIG. 3 shows an exploded view of the first bone screw 106, which further illustrates the attachment of the pawl 116 to the set screw 114. As illustrated, the retaining ring 118 is a circular, flexible piece of material with a cut portion 124 to allow expansion of the diameter of the retaining ring 118. The set screw 114 has a circular boss 128 that includes a retaining ring groove 130, and a threaded portion 132. The pawl 116 has a circular bore 126 that communicates with the circular boss 128 on the set screw 114. The pawl 116 slides over the circular boss 128 and the retaining ring 118 is captured in a retaining ring groove 130 to attach the pawl 116 to the set screw 114 without restraining the rotation of the pawl 116.

In use, first bone screw 106 can be inserted into a bony portion of a patient's spine, such as the posterior arch, pedicle, or vertebral body of a vertebra. Then, toothed rod 102 can be placed into a recess 134 in screw head 112. The set screw 114 can be threaded into the screw head 112 until there is significant engagement of the pawl 116 with the ratchet teeth 104 of the toothed rod 102. Distracting or compressing forces, depending on the orientation of the pawl 116, can then be used to slide the first bone screw 106, and therefore the vertebra to which it is attached, relative to toothed rod 102.

Figure 4:
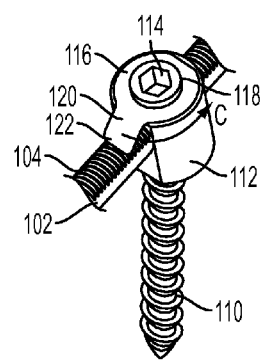
FIG. 4 illustrates a screw of the example of FIG. 2 in a first orientation.
Figure 5:
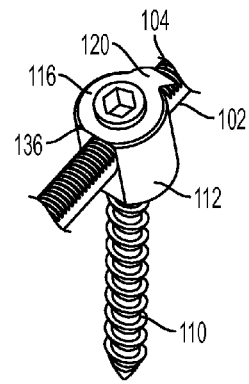
FIG. 5 illustrates a screw of the example of FIG. 2 in a second, or reversed, orientation.
Figure 6:
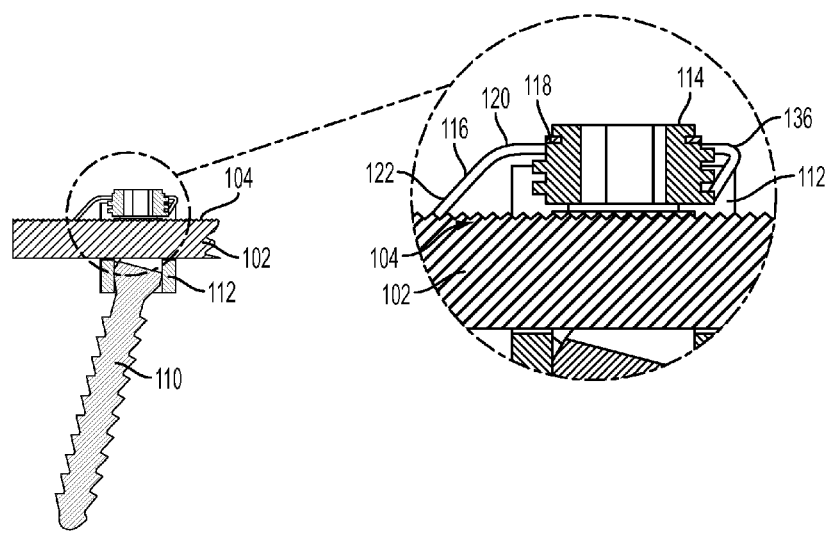
FIG. 6 illustrates a screw of the example of FIG. 2 in a sectioned view with an enlarged region to illustrate the ratchet and pawl mechanism.

FIG. 4 illustrates that rotation of the pawl 116 in the direction of the arrow C can reverse the direction of travel of first bone screw 106 by changing to the orientation shown in FIG. 5. The pawl 116 is rotatable from a first position, as shown in FIG. 4, to a second position, as shown in FIG. 5, that is about 180° from the first position. The pawl 116 can include a locking boss 136, which can prevent inadvertent rotation of the pawl 116. The locking boss 136 can allow rotation of the pawl 116 when the set screw 114 is loosened an amount sufficient for the locking boss 136 to clear the screw head 112. After the first bone screw 106 has been moved along toothed rod 102 to a desired location, the set screw 114 can be tightened to rigidly secure the screw head 112 to the toothed rod 102. FIG. 6 shows a sectioned view of the first bone screw 106 with an enlargement to further illustrate the elements of the first bone screw 106 as described above.

Figure 7:
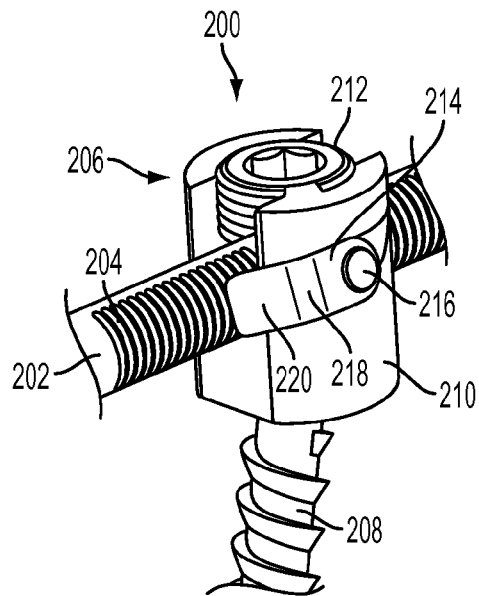
FIG. 7 illustrates a second example of a screw-rod construct of the present technology in a first orientation.
Figure 8:
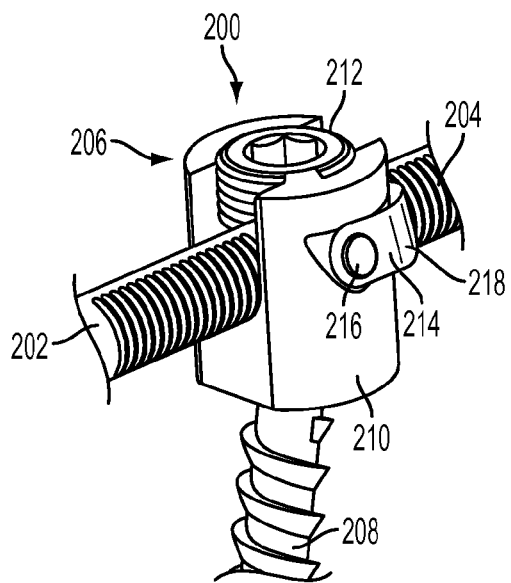
FIG. 8 illustrates a screw of the example of FIG. 7 in a second, or reversed, orientation.

FIGS. 7 and 8 illustrate a second example of a screw-rod construct of the present technology. Screw-rod construct 200 as shown in FIGS. 7 and 8 includes a toothed rod 202 having ratchet teeth 204, and a bone screw 206. The bone screw 206 has a threaded shaft 208, a screw head 210, a set screw 212, and a pawl 214. The pawl 214 can be rotatably mounted to a side of the screw head 210 by a fastener 216, such as a pin. The pawl 214 includes a bend 218 and a blade 220. The blade 220 of the pawl 214 engages the ratchet teeth 204 of the toothed rod 202. Rotation of the pawl 214 from a first position, as shown in FIG. 7, to a second position, as shown in FIG. 8, that is about 180° from the first position, can reverse the direction of travel of the bone screw 206 along the length of the toothed rod 202.

Figure 9:
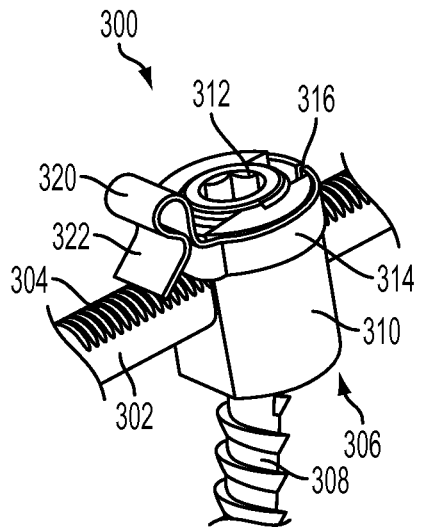
FIG. 9 illustrates a third example of a screw-rod construct of the present technology in a first orientation.
Figure 10:
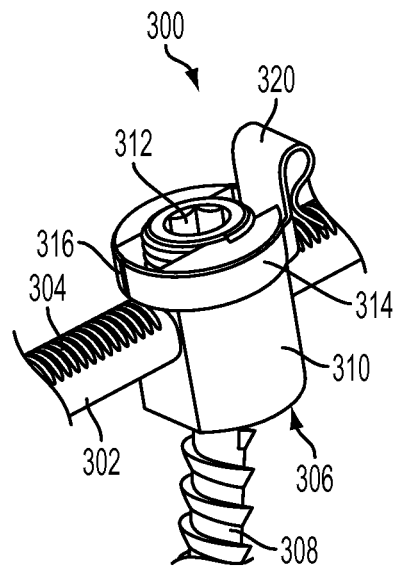
FIG. 10 illustrates a screw of the example of FIG. 9 in a second, or reversed, orientation.
Figure 11:
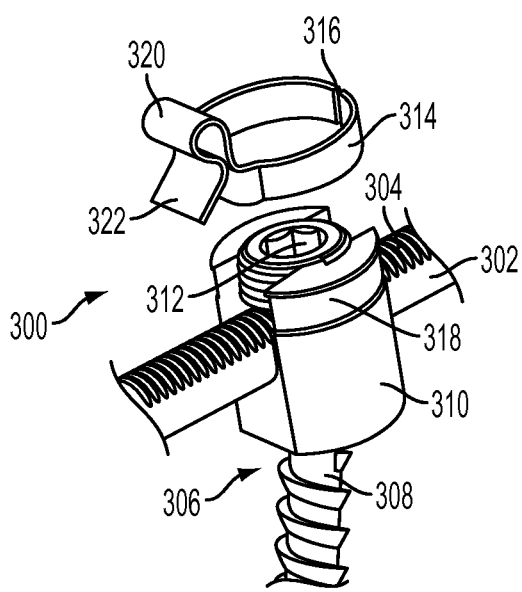
FIG. 11 illustrates an exploded view of a screw of the example of FIG. 9.

FIGS. 9 through 11 illustrate a third example of a screw-rod construct of the present technology, with FIG. 11 showing an exploded view. Screw-rod construct 300 as shown in FIGS. 9 through 11 includes a toothed rod 302 having ratchet teeth 304, and a bone screw 306. The bone screw 306 has a threaded shaft 308, a screw head 310 having a pawl receiving groove 318, a set screw 312, and a pawl 314. The pawl 314 is a clip-on pawl that can be connected to the screw head 310 by being received by the pawl receiving groove 318 of the screw head 310. Pawl 314 can include a cut 316 that allows expansion of the diameter of the pawl 314 to facilitate installation of the pawl 314 onto the pawl receiving groove 318 of the screw head 310. The pawl 314 can include a spring portion 320 and a blade 322. The blade 322 engages the ratchet teeth 304 of the toothed rod 302. The spring portion 320 can provide flexibility to the pawl 314 to allow the blade 322 to slide over the ratchet teeth 304 of the toothed rod 302 when the bone screw 306 is ratcheted along the length of the toothed rod 302. Rotation of the pawl 314 from a first position, as shown in FIG. 9, to a second position, as shown in FIG. 10, that is about 180° from the first position, can reverse the direction of travel of the bone screw 306 along the length of the toothed rod 302.

Figure 12:
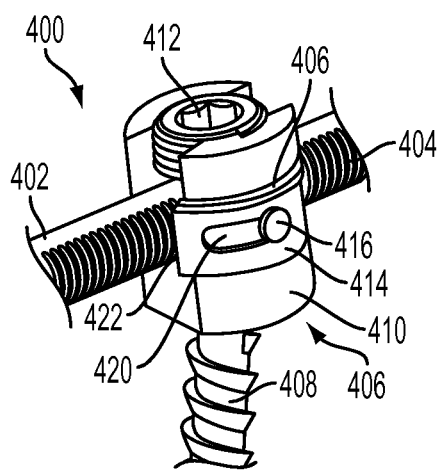
FIG. 12 illustrates a fourth example of a screw-rod construct of the present technology in a first orientation.
Figure 13:
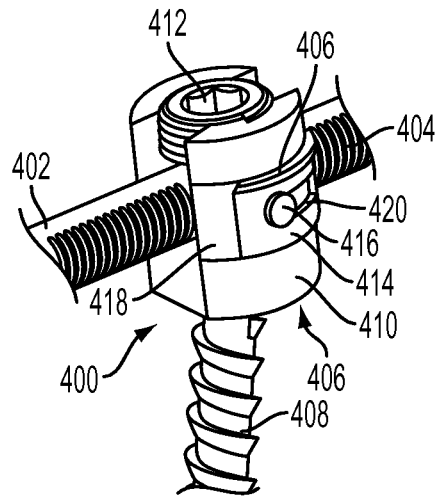
FIG. 13 illustrates a screw of the example of FIG. 12 in a second, or reversed, orientation.

FIGS. 12 and 13 illustrate a fourth example of a screw-rod construct of the present technology. Screw-rod construct 400 as shown includes a toothed rod 402 having ratchet teeth 404, and a bone screw 406. The bone screw 406 has a threaded shaft 408, a screw head 410, a set screw 412, and a sliding pawl 414. The sliding pawl 414 can be slidably attached to the screw head 410 with a fastener 416, such as a pin. The pawl 414 can also include a fastener groove 420, and the fastener 416 can extend through the fastener groove 420 to slidably attach the pawl 414 to the screw head 410. The screw head 410 can include a pawl receiving groove 418 on a side of the screw head 410, and sliding pawl 414 can be slidably received in the pawl receiving groove 418. The pawl 414 can further include a first blade 422 at one first end, and a second blade 422 (not shown) at the opposite end. The first blade 422 can engage the ratchet teeth 404 of the toothed rod 402 when the slidable pawl 414 is in a first position, as shown in FIG. 12, allowing the bone screw 406 to ratchet along the length of the toothed rod 402 in one direction. The second blade 422, which can be a mirror image of the first blade 422, can engage the ratchet teeth 404 of the toothed rod 402 when the slidable pawl 414 is in a second position, as shown in FIG. 13, allowing the bone screw 406 to ratchet along the length of the toothed rod 402 in the opposite direction.

Figure 14:
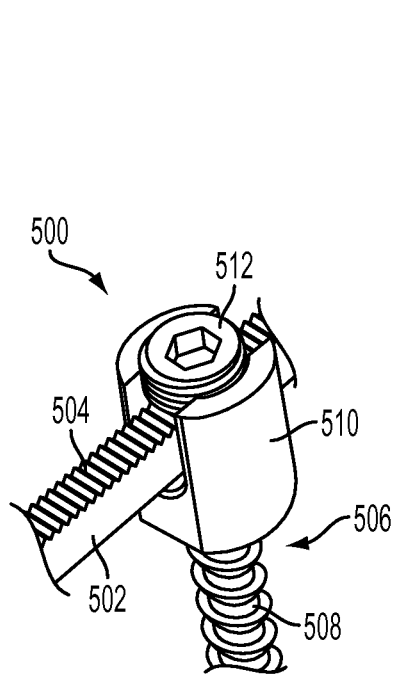
FIG. 14 illustrates a fifth example of a screw-rod construct of the present technology in a first orientation.
Figure 15:
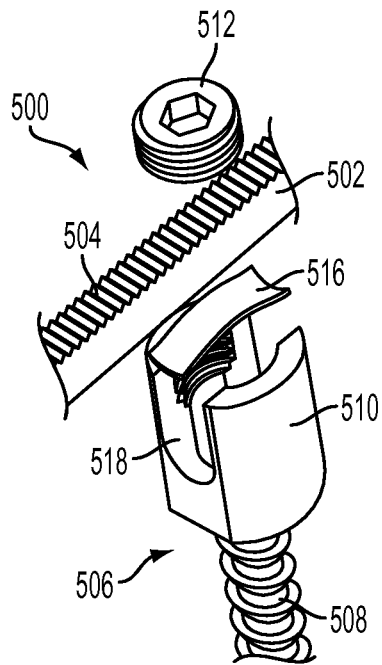
FIG. 15 shows an exploded view of the screw of the example of FIG. 14.
Figure 16:
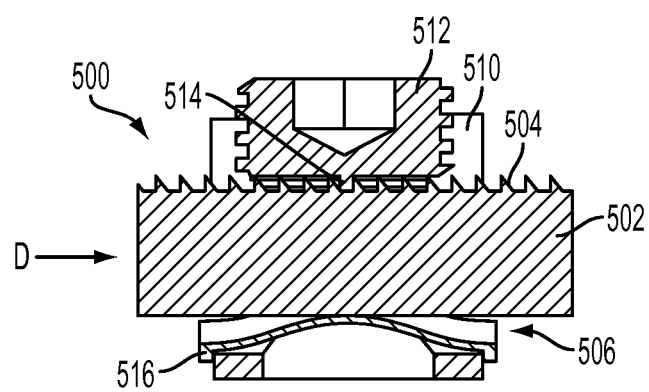
FIG. 16 illustrates a cross sectional view of the screw of the example of FIG. 14.

FIGS. 14 through 16 illustrate a fifth example of a screw-rod construct of the present technology, with FIG. 15 being an exploded view and FIG. 16 being a cross-sectional view. Screw-rod construct 500 includes a toothed rod 502 having ratchet teeth 504, and a bone screw 506. The bone screw 506 has a threaded shaft 508, a screw head 510, a set screw 512, and a pawl 514. The pawl 514 can be a raised boss on the bottom surface of the set screw 512 that engages the ratchet teeth 504 of the toothed rod 502. A leaf spring 516 can be positioned under the rod receiving groove 518 of the screw head 510, and can provide an upward force on the toothed rod 502 to ensure engagement of the ratchet teeth 504 and the pawl 514. When horizontal force is exerted in the direction of arrow D, the leaf spring 516 can deflect out of the way and allow ratcheting of the bone screw 506 along the length of the toothed rod 502.

Figure 17:
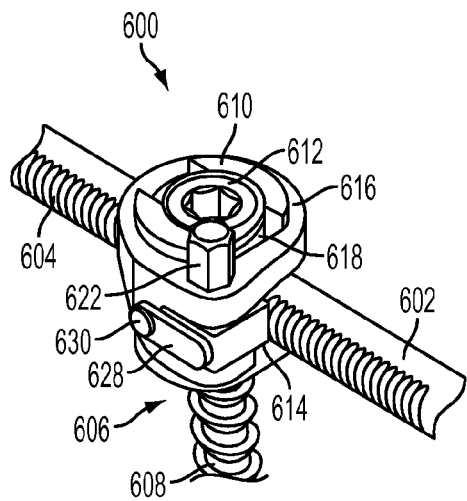
FIG. 17 illustrates a sixth example of a screw-rod construct of the present technology in a first orientation.
Figure 18:
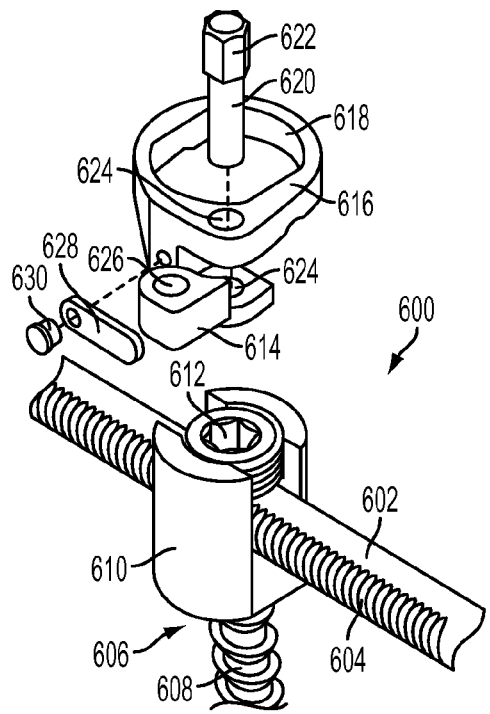
FIG. 18 illustrates an exploded view of the screw of the example of FIG. 17.

FIGS. 17 and 18 illustrate a sixth example of a screw-rod construct of the present technology, with FIG. 18 being an exploded view. Screw-rod construct 600 includes a toothed rod 602 having ratchet teeth 604, and a bone screw 606. The bone screw 606 has a threaded shaft 608, a screw head 610, a set screw 612, and a pawl 614. The pawl 614 is attached to a frame 616 that has a recess 618. The recess 618 attaches to the screw head 610, and can be lowered over the screw head 610 into alignment with the toothed rod 602 so that the pawl 614 engages the ratchet teeth 604 of the toothed rod 602. The pawl 614 can be attached to the frame 616 with a fastener 620, such as a pin, that extends through a bore 624 in the frame 616 and can be rigidly attached to the pawl 614 due to press fit of the fastener 620 into a pawl hole 626 in the pawl 614. As illustrated, the fastener 620 can have a hexagonal head 622. A spring 628 can be attached to the frame 616 by a spring fastener 630, and can exert an inward force on the pawl 614 to maintain engagement of the pawl 614 with the ratchet teeth 604. To disengage the pawl 614 from the ratchet teeth 604, an operator can rotate the hexagonal head 622 of the fastener 620 clockwise.

Figure 19:
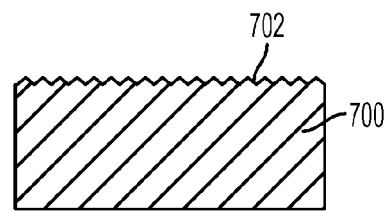
FIG. 19 illustrates a sectioned view of one example of teeth on a rod of the present technology having triangular ratchet teeth cut into the rod.
Figure 20:
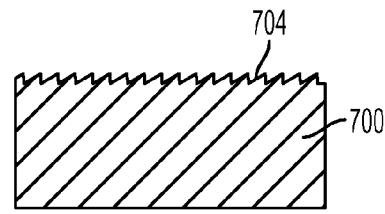
FIG. 20 illustrates a sectioned view of a second example of teeth on a rod of the present technology having sawtooth ratchet teeth cut into the rod.
Figure 21:
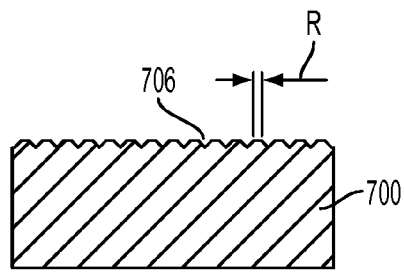
FIG. 21 illustrates a sectioned view of a third example of teeth on a rod of the present technology having spaced ratchet teeth cut into the rod.
Figure 22:
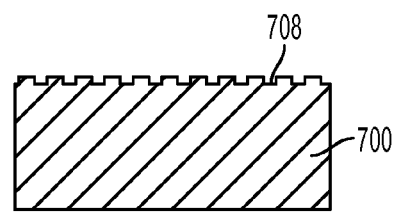
FIG. 22 illustrates a sectioned view of a fourth example of teeth on a rod of the present technology having square ratchet teeth cut into the rod.
Figure 23:
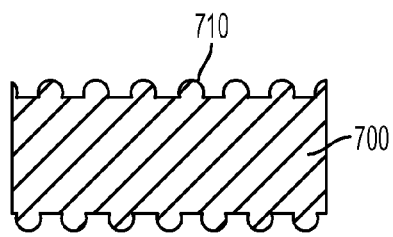
FIG. 23 illustrates a sectioned view of a fifth example of teeth on a rod of the present technology having a helical coil sintered, welded, soldered, bonded or otherwise attached to the rod.
Figure 24:
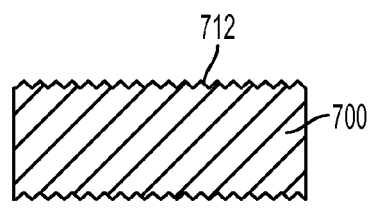
FIG. 24 illustrates a sectioned view of a sixth example of teeth on a rod of the present technology having helical threads cut into the rod.

FIGS. 19 through 24 illustrate examples of ratchet teeth that can be formed on a toothed rod 700 of the present technology. The ratchet teeth can be formed on the toothed rod 700 in any suitable manner, such as by being cut, pressed, rolled, forged, molded or otherwise formed. In one example, toothed rod 700 having ratchet teeth can be fabricated in a molding operation such as MIM (Metal Injection Molding). In other examples, ratchet teeth can be formed by waterjet cutting, EDM (Electrical Discharge Machining), etching, or ECM (Electrochemical Machining). FIG. 19 shows toothed rod 700 having triangular teeth 702. FIG. 20 shows toothed rod 700 having saw teeth 704. FIG. 21 shows toothed rod 700 having triangular teeth 706 in a staggered pattern, wherein the ratchet teeth 706 are separated by an offset R. FIG. 22 shows toothed rod 700 having squared teeth 708. FIG. 23 shows toothed rod 700 having ratchet teeth formed by a helical piece of material 710 that is wrapped around and secured to the toothed rod 700. The helical piece of material 710 can be secured to the toothed rod in any suitable manner, including, for example, being sintered, welded, soldered, or bonded. FIG. 24 shows toothed rod 700 having ratchet teeth formed by helical threads 712. Helical threads 712 can be formed in any suitable manner, including being cut into toothed rod 700, or being formed by a thread rolling operation which could increase the fatigue life of toothed rod 700.

Figure 25:
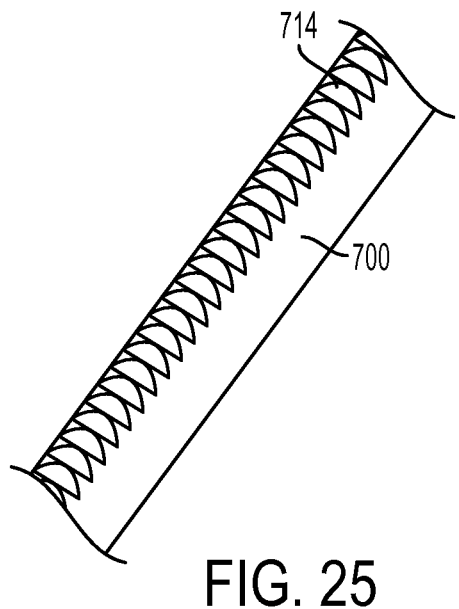
FIG. 25 illustrates a perspective view of one example of a rod of the present technology having ratchet teeth cut straight across the rod.
Figure 26:
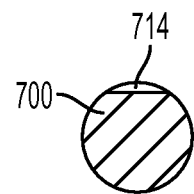
FIG. 26 illustrates a sectioned view of the example of a rod illustrated in FIG. 25.
Figure 27:
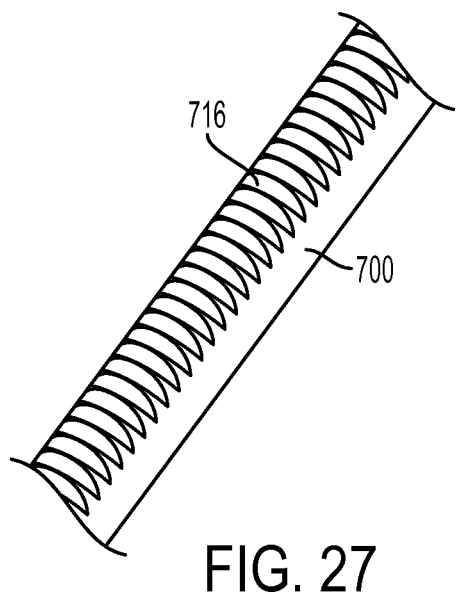
FIG. 27 illustrates a perspective view of a second example of a rod of the present technology having ratchet teeth cut radially on the rod.
Figure 28:
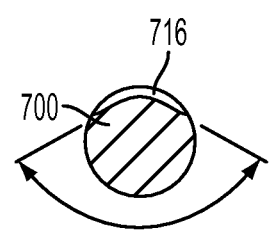
FIG. 28 illustrates a sectioned view of the example of a rod illustrated in FIG. 27.

FIGS. 25 and 26 illustrate toothed rod 700 having triangular teeth 714 formed straight, meaning on a linear path, across an outer surface of the toothed rod 700. FIGS. 27 and 28 illustrate toothed rod 700 having triangular teeth 716 formed radially, meaning on a non-linear, arcuate path, across an outer surface of the toothed rod 700.

Figure 29:
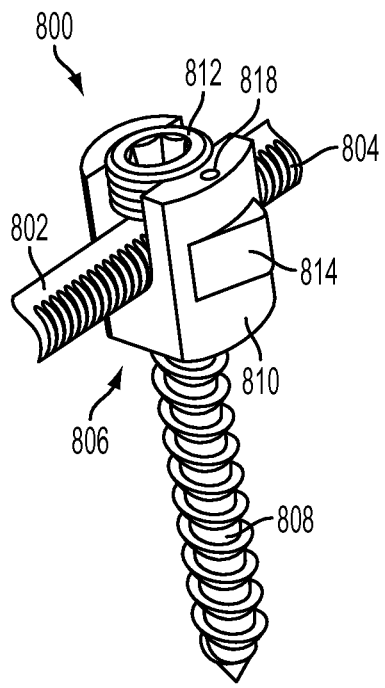
FIG. 29 illustrates a seventh example of a screw-rod construct of the present technology.
Figure 30:
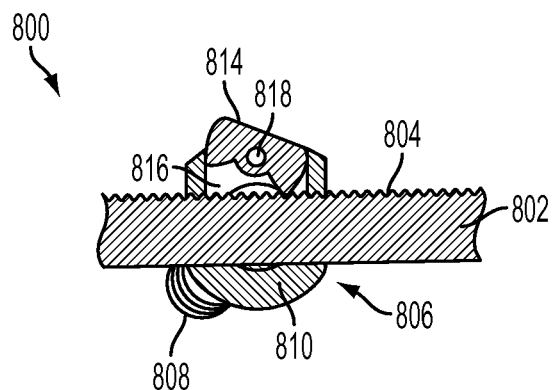
FIG. 30 illustrates a sectioned view of the screw-rod construct illustrated in FIG. 29.

FIGS. 29 and 30 illustrate a seventh example of a screw-rod construct of the present technology, with FIG. 30 being sectioned view. Screw-rod construct 800 includes a toothed rod 802 having ratchet teeth 804, and a bone screw 806. The bone screw 806 has a threaded shaft 808, a screw head 810, a set screw 812, and a pawl 814. The pawl 814 is a toggle pawl located in a side of the screw head 810. The toggle pawl 814 is housed within a recess 816 in the side of the screw head 810. The toggle pawl 814 is attached to the screw head 810, preferably at the center of the toggle pawl 814, by a fastener 818, such as a pin. The toggle pawl 814 can rotate about the fastener, from a first position, as shown in FIG. 30, to a second position that has an orientation opposite that of the first position, thus allowing the bone screw 806 to be ratcheted along the length of the toothed rod 802 in a first or second direction, respectively. The toggle pawl 814 can be spring-loaded, or can have sufficient friction to allow it to be rotated from the first position to the second position by manual force exerted by an operator.

Figure 31:
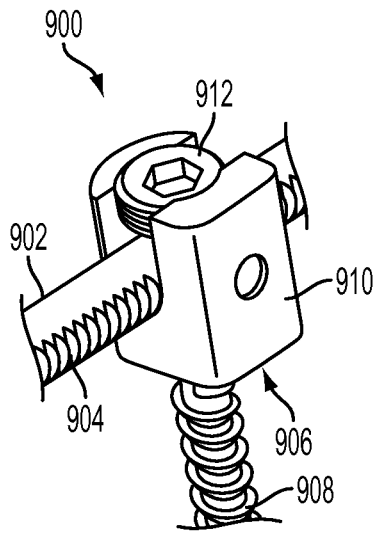
FIG. 31 illustrates an eighth example of a screw-rod construct of the present technology.
Figure 32:
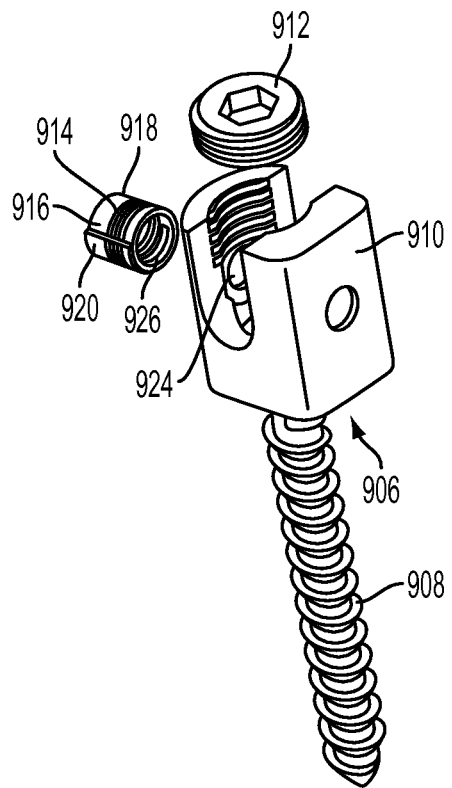
FIG. 32 illustrates an exploded view of the screw-rod construct illustrated in FIG. 31.
Figure 33:
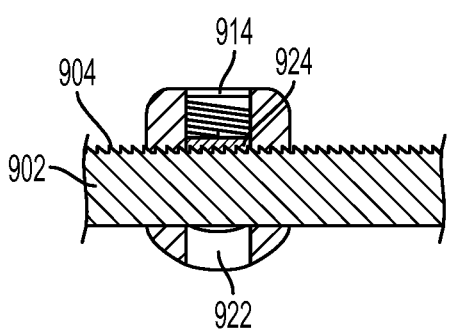
FIG. 33 illustrates a sectioned view of the screw-rod construct illustrated in FIG. 31.

Previously described are pawls which flex or rotate, however it should be understood that a pawl may also translate linearly away from toothed rod and return to contact with toothed rod under the action of a spring such as a helical spring, a leaf spring, a machined spring, or any elastic resilient material. FIGS. 31 through 33 illustrate one example of a screw-rod construct of the present technology having such a linearly translating pawl, with FIG. 32 being an exploded view, and FIG. 33 being a sectioned view. Screw-rod construct 900 includes a toothed rod 902 having ratchet teeth 904, and a bone screw 906. The bone screw 906 has a threaded shaft 908, a screw head 910, a set screw 912, and a pawl 914. The pawl 914 is attached to a side of the screw head 910, and can be located in a screw head bore 922 that has a keyway 924. The pawl 914 is a plunger pawl, having teeth 916, a blind hole 926, a helical cut 918, and an anti-rotation boss 920. Helical cut 918 allows plunger pawl 914 to compress like a helical spring. In lieu of helical cut 918, plunger pawl 914 could incorporate a wire wound helical spring, a leaf spring or other resilient material. The anti-rotation boss 920 of the plunger pawl 914 can align with the keyway 924 of the screw head 910 to maintain alignment of plunger pawl 914 with the ratchet teeth 904 of the toothed rod 902. As the bone screw 906 is ratcheted along the length of the toothed rod 902, the helical spring 918 can compress and extend to so that plunger pawl 914 maintains contact with toothed rod 902 and allows motion in one direction only.

Screw-rod constructs including at least one bone screw of the present technology and at least one rod of the present technology can allow compressive or distractive forces to be applied sequentially across each level of a given construct as desired.

In at least one example, the application of compressive or distractive forces can be accomplished by first attaching at least one bone screw of the present technology to at least one desired bony portion of a patient's spine. In one example a first bone screw can be attached to a first bony portion of a patient's spine, and a second bone screw can be attached to a second bony portion of a patient's spine. At least one of the bone screws, or both, can have a pawl. The toothed rod of the present technology can be optionally shaped by an operator, such as a surgeon, and can be attached to each bone screw. In some examples, the toothed rod can be attached to each bone screw by placing the toothed rod in the screw head of the first bone screw and in the screw head of the second bone screw, and then placing a first set screw on the screw head of the first screw and a second set screw on the screw head of the second screw to maintain the toothed rod in the screw head of each bone screw. The pawl of the at least one bone screw having a pawl can be oriented to engage the ratchet teeth of the toothed rod. In some examples, the pawl can be oriented to engage the ratchet teeth of the toothed rod in a first position or a second position, for the application of either distractive or compressive forces as desired. The bone screw having a pawl, or at least one of the bone screws having a pawl, can then be ratcheted along the length of the toothed rod to apply the desired amount of distractive or compressive force. Once the desired amount of distractive or compressive force is achieved, each set screw can be tightened to maintain each bone screw in a fixed position relative to the toothed rod. The distractive or compressive force can be maintained temporarily or permanently.

The distractive or compressive force can be used to alter the distance between bony portions of a patient's spine. For example, the distance between spinal vertebrae of a patient can be altered by attaching a first bone screw to a first spinal vertebra and attaching a second bone screw to a second spinal vertebra, wherein at least the first bone screw has a pawl. A toothed rod can then be attached to the first and second bone screws, and the pawl of the first bone screw can be oriented to engage the ratchet teeth of the toothed rod. The method can then include altering the distance between the first vertebra and the second vertebra. The distance between the first vertebra and the second vertebra can be altered by ratcheting the first bone screw a desired amount along the length of the toothed rod to apply an amount of distractive or compressive force sufficient to obtain the desired altered distance between the first vertebra and the second vertebra. The altered distance can then be maintained, temporarily or permanently, by the pawl engaging the ratchet teeth of the toothed rod.

Figure 34:
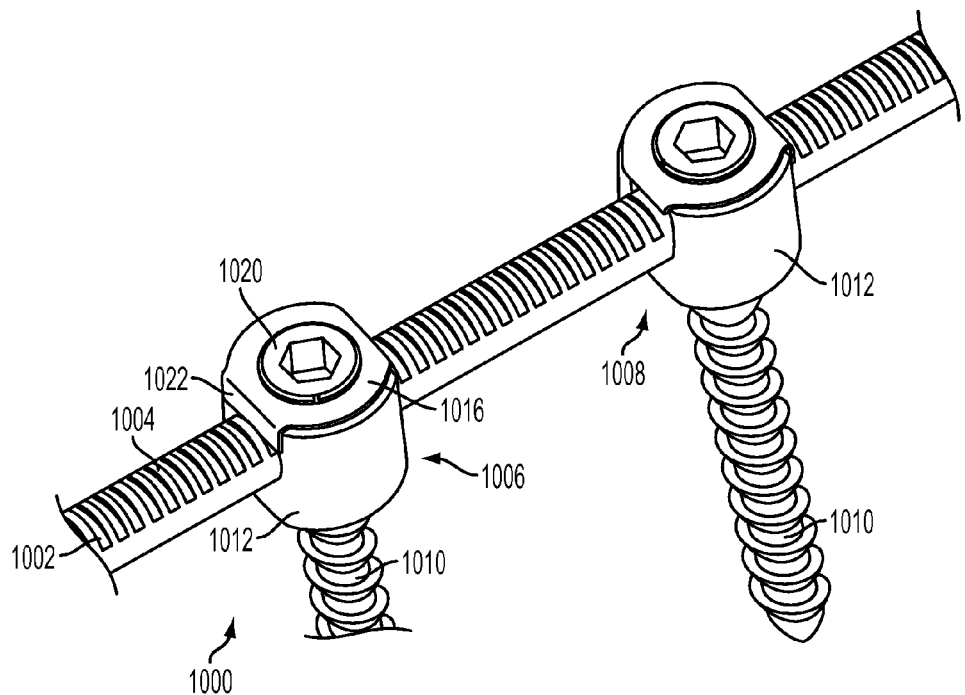
FIG. 34 illustrates a perspective view of a ninth example of a screw-rod construct according to an embodiment of the present technology.
Figure 35:
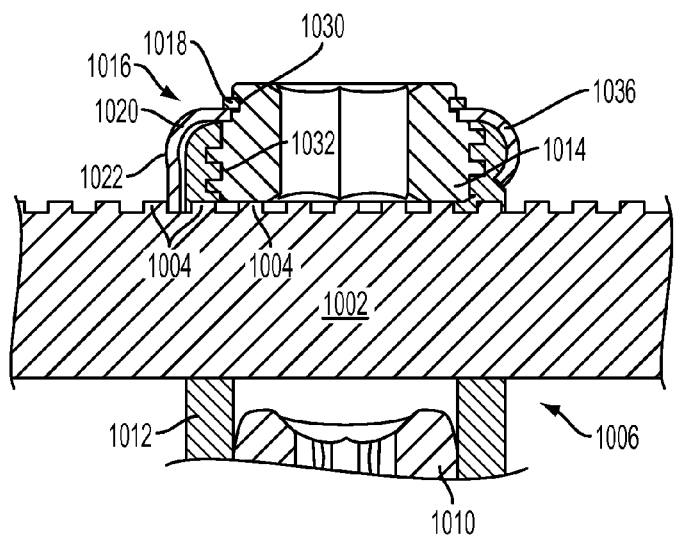
FIG. 35 illustrates a sectional view of the screw-rod construct illustrated in FIG. 34.

FIGS. 34 and 35 illustrate a ninth example of a screw-rod construct 1000 according to an embodiment of the present technology. As shown, the screw-rod construct 1000 includes a toothed rod 1002 having ratchet teeth 1004, and first and second bone screws 1006, 1008, respectively. In the illustrated example of FIG. 34, each bone screw 1006, 1008 includes a threaded shaft 1010, a screw head 1012, a set screw 1014, and a pawl 1016. A retaining ring 1018 is arranged to be received on each set screw 1014 to retain the pawl 1016 on the set screw 1014. The pawl 1016 may be flexible, and includes a bend 1020 and a blade 1022. The portion of the pawl 1014 disposed about the set screw 1012 is shown in the depicted embodiment as being substantially perpendicular to the blade 1022.

When the toothed rod 1002 is coupled to the first bone screw 1006 and the second bone screw 1008, the blade 1022 of each pawl 1016 of each bone screw 1006, 1008 engages at least one tooth of the ratchet teeth 1004 on toothed rod 1002. As depicted in FIGS. 34 and 35, the first bone screw 1006 can be ratcheted along the toothed rod 1002 in a first direction (to the right in FIGS. 34 and 35), but the engagement of the blade 1022 of the first bone screw 1006 with the ratchet teeth 1004 of the toothed rod 1002 can prevent movement of the first bone screw 1006 in the opposite direction. Likewise, the second bone screw 1008 can be ratcheted along the toothed rod 1002 in a second direction (to the left in FIG. 34), but the engagement of the blade 1022 of the second bone screw 1008 with the ratchet teeth 1004 of the toothed rod 1002 can prevent movement of the second bone screw 1008 in the opposite direction. Alternatively, by rotating the pawls 1016 of each bone screw 1006, 1008 180°, the allowed directions of movement of each bone screw 1006, 1008 can be reversed.

FIG. 35 shows a sectional view of the first bone screw 1006 with an enlargement to further illustrate the elements of the first bone screw 1006 as described above. As illustrated, the retaining ring 1018 is a circular, flexible piece of material with a cut portion to allow expansion of the diameter of the retaining ring 1018. The set screw 1014 has a circular boss that includes a retaining ring groove 1030, and a threaded portion 1032. The pawl 1016 has a circular bore 1026 that communicates with the circular boss on the set screw 1014. The pawl 1016 slides over the circular boss and the retaining ring 1018 is captured in the retaining ring groove 1030 to attach the pawl 1016 to the set screw 1014 without restraining the rotation of the pawl 1016. The pawl 1016 is rotatable from a first position, as shown in FIGS. 34 and 35, to a second position (not shown) that is about 180° from the first position. The pawl 1016 can include a locking boss or extension 1036, which can prevent inadvertent rotation of the pawl 1016. The locking boss 1036 can allow rotation of the pawl 1016 when the set screw 1014 is loosened an amount sufficient for the locking boss 1036 to clear the screw head 1012. After the first bone screw 1006 has been moved along toothed rod 1002 to a desired location, the set screw 1014 can be tightened to rigidly secure the screw head 1012 to the toothed rod 1002.

Figure 36:
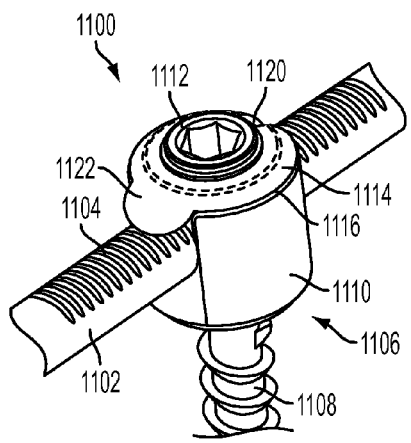
FIG. 36 illustrates a perspective view of a tenth example of a screw-rod construct according to an embodiment of the present technology in a first orientation.
Figure 36A:
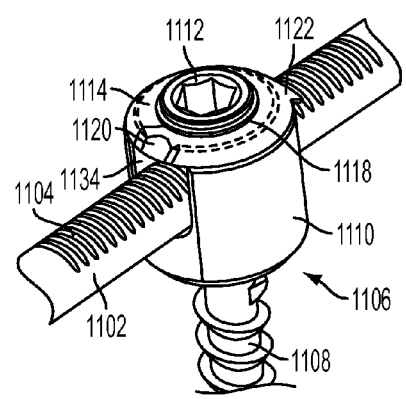
FIG. 36a illustrates a perspective view of the screw-rod construct illustrated in FIG. 36 with the pawl in a second, or reversed, orientation.
Figure 36B:
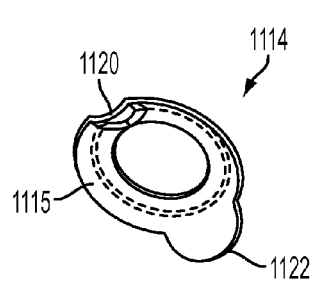
Figure 37:
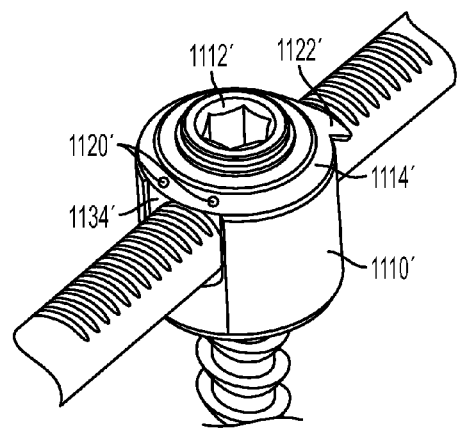
FIG. 37 illustrates a perspective view of another example of the pawl of the screw-rod construct illustrated in FIG. 36 with the pawl shown in the second, or reversed, orientation.

FIGS. 36, 36a, and 36b illustrate a tenth example of a screw-rod construct 1100 according to an embodiment of the present technology. The screw-rod construct 1100 includes a toothed rod 1102 having ratchet teeth 1104, and a bone screw 1106. In the illustrated example of FIG. 36, the bone screw 1106 includes a threaded shaft 1108, a screw head 1110, a set screw 1112, and a pawl 1114. The set screw 1112 of the bone screw 1106 includes a retaining ring 1118, which retains the pawl 1114 on the set screw 1112. The screw head 1110 includes a chamfered top portion 1116 and the pawl 1114 also includes an angled annular portion 1115 about the periphery thereof (see FIG. 36b) for engaging the chamfered top portion 1116 of the screw head 1110. The pawl 1114 includes a blade 1122 for engaging the ratchet teeth 1104 on the toothed rod 1102. The pawl 1114 is rotatable from a first position, as shown in FIG. 36, to a second position, as shown in FIG. 36a, that is about 180° from the first position. The pawl 1114 can include a detent 1120 on a side of the pawl opposite the blade 1122, which can be received in a rod receiving recess 1134 to prevent inadvertent rotation of the pawl 1114. The detent 1120 can allow rotation of the pawl 1114 when the set screw 1112 is loosened an amount sufficient for the detents to clear the screw head 1110. After the bone screw 1106 has been moved along toothed rod 1102 to a desired location, the set screw 1112 can be tightened to rigidly secure the screw head 1110 to the toothed rod 1102. As shown in FIG. 37, a slightly modified pawl 1114' includes a plurality of detents 1120' spaced from one another on a side of the pawl 1114' opposite the blade 1122'. The detents 1120' can be received in a rod receiving recess 1134' of screw head 1110' to prevent inadvertent rotation of the pawl 1114' about set screw 1112'.

Figure 38:
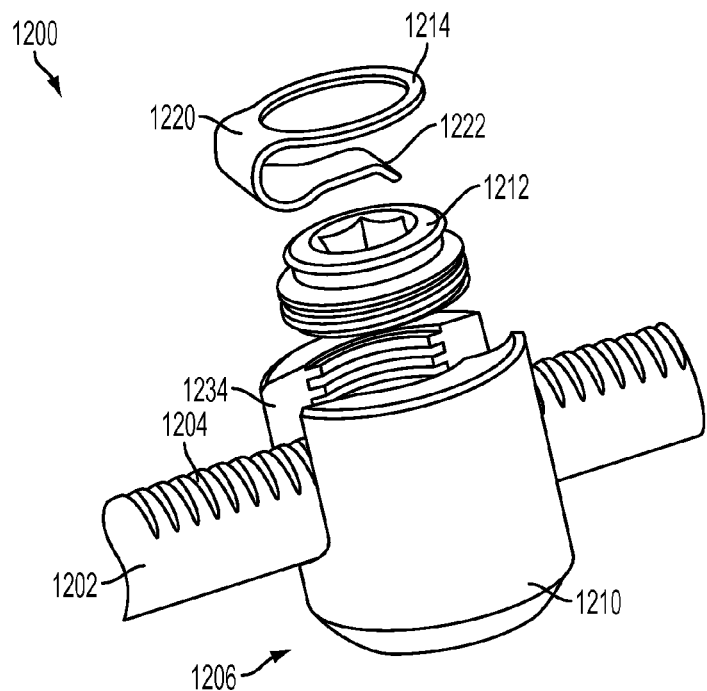
FIG. 38 illustrates an exploded perspective view of an eleventh example of a screw-rod construct according to an embodiment of the present technology.
Figure 39:
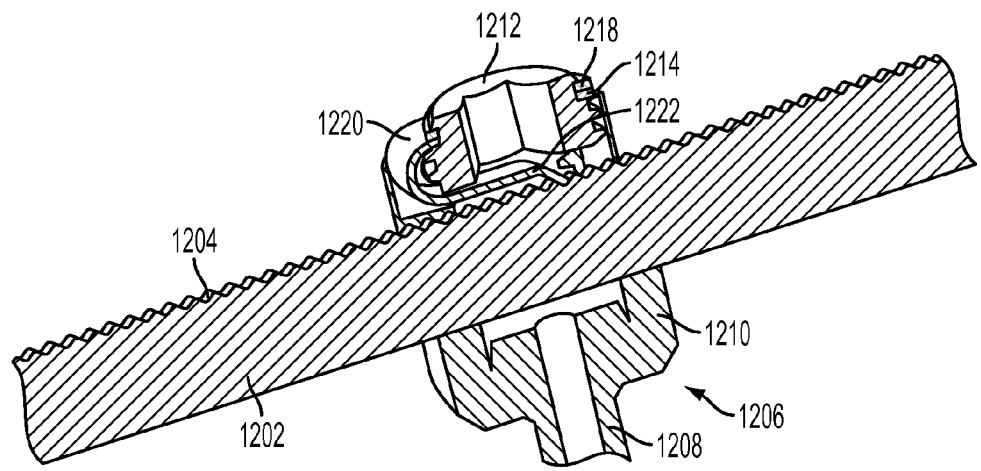
FIG. 39 illustrates a sectional assembled view of the screw-rod construct illustrated in FIG. 38.

FIG. 38 illustrates an exploded perspective view of an eleventh example of a screw-rod construct 1200 according to an embodiment of the present technology. FIG. 39 illustrates a sectional assembled view of the screw-rod construct 1200 illustrated in FIG. 38. The screw-rod construct 1200 includes a toothed rod 1202 having ratchet teeth 1204, and a bone screw 1206 including a threaded shaft 1208, a screw head 1210, a set screw 1212, and a pawl 1214. The set screw 1212 of the bone screw 1206 includes a retaining ring 1218, which retains the pawl 1214 on the set screw 1212. The pawl 1214 may be flexible, and includes a bend 1220 and a blade 1222.

When the toothed rod 1202 is received in rod receiving recess 1234 of the bone screw 1206, the blade 1222 of the pawl 1214 extends underneath the set screw 1212 and engages at least one tooth of the ratchet teeth 1204 on toothed rod 1202. The bone screw 1206 can be ratcheted along the toothed rod 1202 in a first direction (to the left in FIG. 34), but the engagement of the blade 1222 of the bone screw 1206 with the ratchet teeth 1204 of the toothed rod 1202 can prevent movement of the bone screw 1206 in the opposite direction. Further tightening of the set screw 1212 rigidly engages the blade 1222 of the pawl 1214 into the ratchet teeth 1204 such that further movement of the bone screw 1206 in any direction is prevented and a rigid connection is established.

Figure 40:
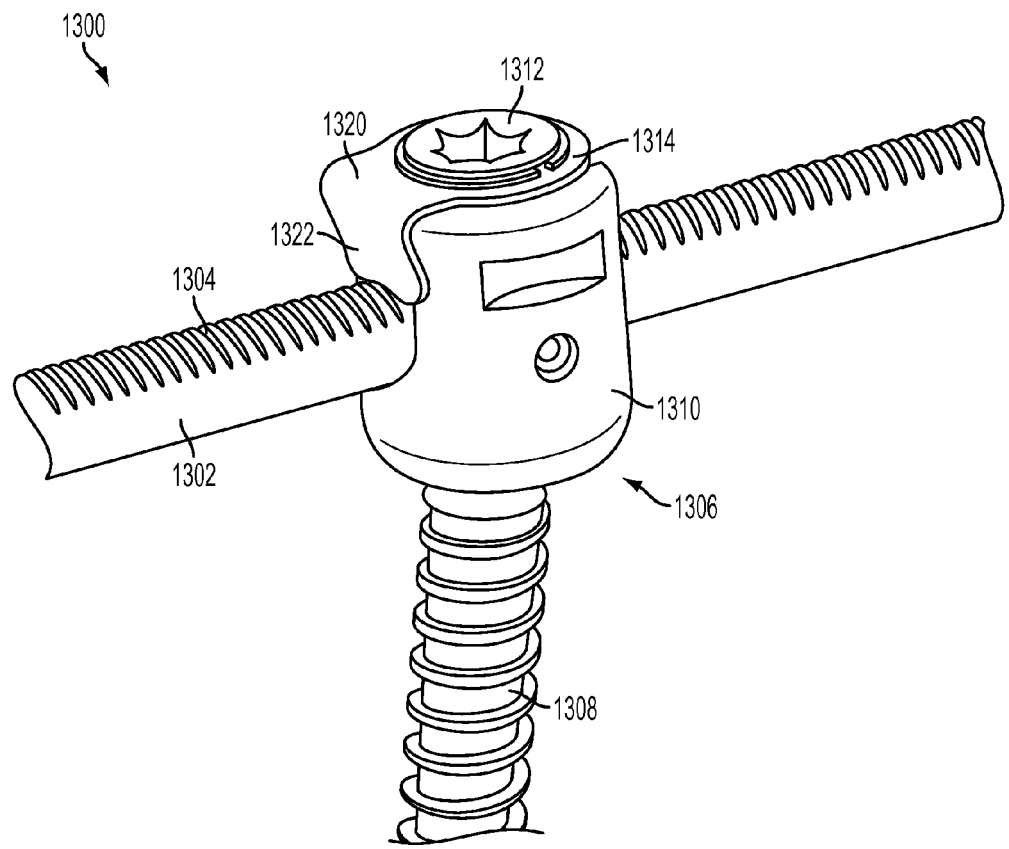
FIG. 40 illustrates a perspective view of a twelfth example of a screw-rod construct according to an embodiment of the present technology.

FIG. 40 illustrates a twelfth example of a screw-rod construct 1300 according to an embodiment of the present technology. The screw-rod construct 1300 includes a toothed rod 1302 having ratchet teeth 1304, and a bone screw 1306 of the present technology including a threaded shaft 1308, a screw head 1310, a set screw 1312, and a pawl 1314. The set screw 1312 includes a retaining ring 1318, which retains the pawl 1314 on the set screw 1312. The pawl 1314 may be flexible, and includes a bend 1320 and a blade 1322. As shown in the embodiment depicted in FIG. 40, an interior angle between the portion of the pawl 1314 disposed about the set screw 1312 and the blade 1322 may be less than 90 degrees.

Figure 41:
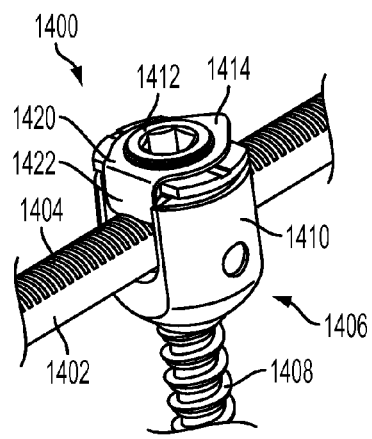
FIG. 41 illustrates a perspective view of a thirteenth example of a screw-rod construct according to an embodiment of the present technology.
Figure 42:
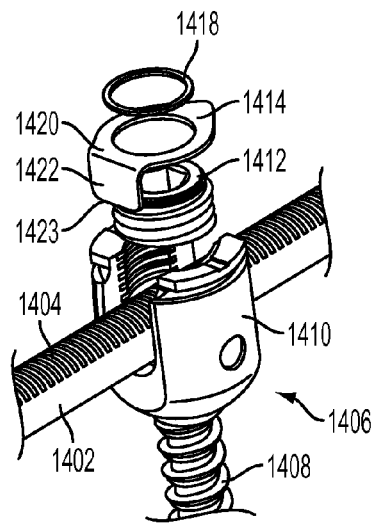
FIG. 42 illustrates an exploded perspective view of the screw-rod construct illustrated in FIG. 41.
Figure 43:
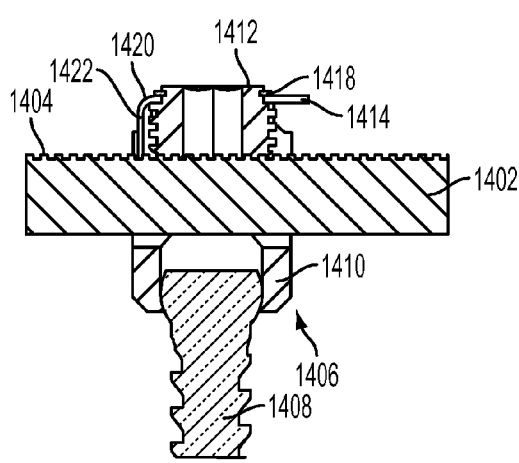
FIG. 43 illustrates a sectional view of the screw-rod construct illustrated in FIG. 41.
Figure 44:
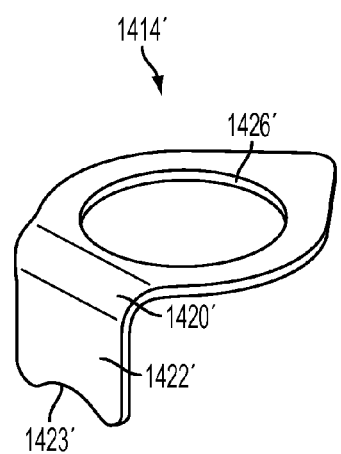
FIG. 44 illustrates a perspective view of another example of the pawl of the screw-rod construct illustrated in FIGS. 41-43.

FIG. 41 illustrates a perspective view of a thirteenth example of a screw-rod construct 1400 according to an embodiment of the present technology. FIG. 42 illustrates an exploded perspective view of the screw-rod construct 1400 illustrated in FIG. 41. FIG. 43 illustrates a sectional view of the screw-rod construct 1400 illustrated in FIG. 41. The screw-rod construct 1400 includes a toothed rod 1402 having ratchet teeth 1404, and a bone screw 1406 of the present technology including a threaded shaft 1408, a screw head 1410, a set screw 1412, and a pawl 1414. The set screw 1412 includes a retaining ring 1418, which retains the pawl 1414 on the set screw 1412. The pawl 1414 may be flexible, and includes a bend 1420 and a blade 1422 configured to engage the ratchet teeth 1404. As shown in the embodiment depicted in FIGS. 41-43, the portion of the pawl 1414 disposed about the set screw 1412 is substantially perpendicular to the blade 1422. An edge 1423 of the blade 1422, which edge is arranged to be received in and engage the ratchet teeth 1404, may be substantially linear as shown in FIGS. 41-43. In fact, the tooth-engaging edge of the pawl blade of any of the embodiments described herein may be substantially linear when, for example, the toothed rod is cut as shown in FIGS. 25-26. Alternatively, the tooth-engaging edge of the pawl blade of any of the embodiments described herein may be substantially curvilinear when, for example, the toothed rod is cut as shown in FIGS. 27-28. For example, as shown in FIG. 44, a tooth-engaging edge 1423' of blade 1422' of pawl 1414' is shown as being curvilinear in order to conform to a non-linear, arcuate path cut across an outer surface of a toothed rod.

Figure 45:
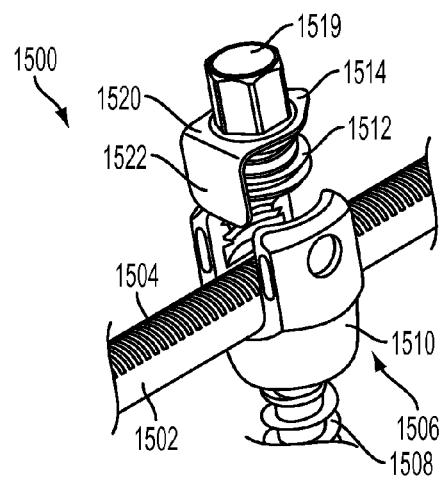
FIG. 45 illustrates a perspective view of a fourteenth example of a screw-rod construct according to an embodiment of the present technology during assembly.
Figure 46:
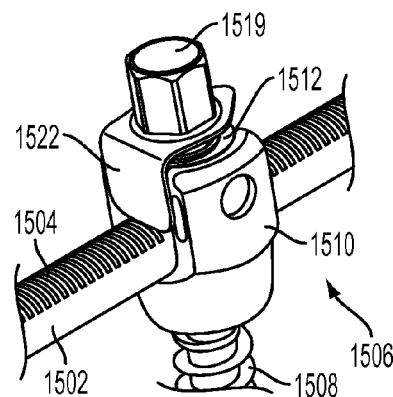
FIG. 46 illustrates a perspective view of the screw-rod construct illustrated in FIG. 45 when assembled.
Figure 47:
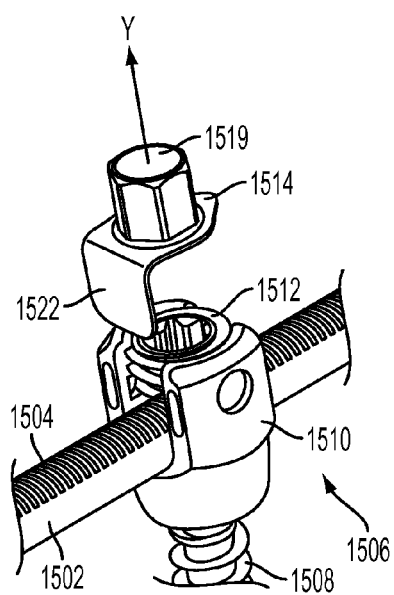
FIG. 47 illustrates a perspective view of the screw-rod construct illustrated in FIG. 45 after assembly and removal of pawl.
Figure 48:
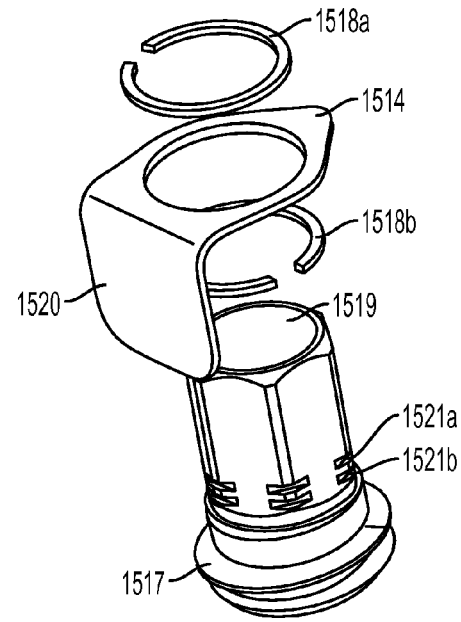
FIG. 48 illustrates an enlarged and exploded detail view of a torque-off set screw of the screw-rod construct illustrated in FIG. 45.

FIGS. 45 through 48 illustrate a fourteenth example of a screw-rod construct 1500 according to an embodiment of the present technology. The screw-rod construct 1500 is substantially similar to the screw-rod construct 1400 described above and shown in FIGS. 41-43, but also includes a torque-off, or frangible, set screw configuration. FIG. 45 illustrates a perspective view of the screw-rod construct 1500 during assembly. FIG. 46 illustrates a perspective view of the screw-rod construct 1500 when assembled. FIG. 47 illustrates a perspective view of the screw-rod construct 1500 after assembly and removal of the pawl 1514. FIG. 48 illustrates an enlarged and exploded detail view of the torque-off set screw 1512 of the screw-rod construct 1500. Referring to FIGS. 45-47, the screw-rod construct 1500 includes a toothed rod 1502 having ratchet teeth 1504, and a bone screw 1506. The bone screw 1506 includes a threaded shaft 1508, a screw head 1510, a set screw 1512, and a pawl 1514. The set screw 1512, as shown in FIG. 48, includes a threaded portion 1517 and an extended, frangible hex portion 1519 having two retaining grooves 1521a, 1521b spaced axially from one another along the outer periphery thereof. The retaining grooves 1521a, 1521b are configured to receive respective first and second retaining rings 1518a, 1518b, which axially retain the pawl 1514 on the hex portion 1519 of the set screw 1512 while allowing rotation of the pawl 1514. The pawl 1514 may be flexible, and includes a bend 1520 and a blade 1522 configured to engage the ratchet teeth 1504. The portion of the pawl 1514 disposed about the set screw 1512 is shown as being substantially perpendicular to the blade 1522 although other angles are possible as shown and disclosed in other embodiments provided herein. The frangible hex portion 1519 of the set screw 1512 may be configured to be broken off from the lower threaded portion of the set screw 1512, for example, upon tightening of the set screw 1512 with a predetermined torque. The predetermined torque may be set according to an amount sufficient to rigidly secure the bone screw 1506 to the toothed rod 1502. Upon such breaking of the frangible hex portion 1519 from the remainder of the set screw 1512, the hex portion 1519 and pawl 1514 may be moved away in direction Y.

The following description of how the compression-distraction spinal fixation system may be used is applicable to any of the foregoing example screw-rod constructs. In use, each bone screw is secured to respective bony portions of a patient's spine. The toothed rod may be shaped by the surgeon and then placed in the screw head of each bone screw in standard fashion. The set screw is then positioned for threaded attachment to the screw head with the pawl oriented in either a compressive (0°) or distractive (180°) direction. The unidirectional pawl is then received in the ratchet teeth of the toothed rod. By manually compressing or distracting adjacent bone screws, the pawl ratchets along the toothed rod, resting within the ratchet teeth and maintaining the desired compressive or distractive force. Once the desired force and position are reached, the set screw is then tightened into the threaded portion of the screw head. In the case of the embodiment depicted in FIGS. 38 and 39, for example, the independently rotatable, ratcheting pawl may gradually retract into a hollow center of the set screw, causing rigid fixation with the underlying rod. In order to bring the pawl into contact with the ratchet teeth of the toothed rod while allowing ratcheted movement of the bone screws along the toothed rod, the set screw may be loosely ("provisionally") threaded to the screw head or may be, for example, received in an initial non-threaded portion (not shown) of the screw head spaced away from the toothed rod sufficiently to allow the pawl to ratchet. The non-threaded portion may include a lip (not shown) on the top of the screw head so that once the set screw is manually pushed across the lip, it is held within the non-threaded portion (between the lip and the threaded portion) during ratcheting.

Figure 49:
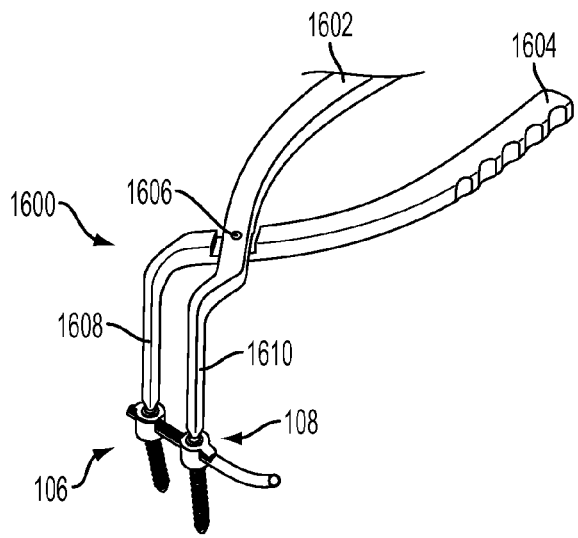
FIG. 49 illustrates a perspective view of a compressor tool according to an embodiment of the present technology, which tool is engaging and manipulating two adjacent bone screws.
Figure 51:
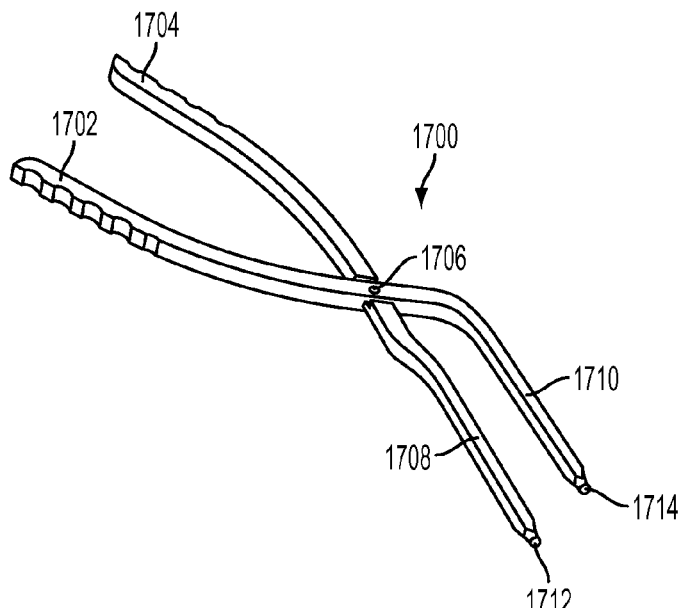
FIG. 51 illustrates a perspective view of a compressor tool according to another embodiment of the present technology.

FIG. 49 illustrates a perspective view of a compressor tool 1600 according to an embodiment. Although compressor tool 1600 is shown engaging and manipulating two adjacent bone screws 106, 108 as shown in the embodiment depicted in FIGS. 2-6, compressor tool 1600 may be used with any of the above-described ratcheting screw-rod constructs. The compressor tool 1600 may include first and second handle portions 1602, 1604 which may be ergonomically formed for gripping by a surgeon. In the manner of a pair of pliers, the first and second handle portions 1602, 1604 may be pivotably coupled to one another at a common fulcrum or pivot pin 1606. The first handle portion 1602 may be connected to a first angled extension portion 1610 and the second handle portion 1604 may be connected to a second angled extension portion 1608. The first and second angled extension portions 1610, 1608 may extend at an angle relative to a plane defined by the first and second handle portions 1602, 1604 such as, for example, in a direction substantially parallel to an axis of the pivot pin 1606 as shown in FIG. 49. FIG. 51 illustrates a perspective view of a modified compressor tool 1700 according to another embodiment of in which first and second angled extension portions 1710, 1708 may extend at about a 45° angle relative to a plane defined by first and second handle portions 1702, 1704 such as, for example, in a direction substantially 45° relative to an axis of a pivot pin 1706.

Figure 50:
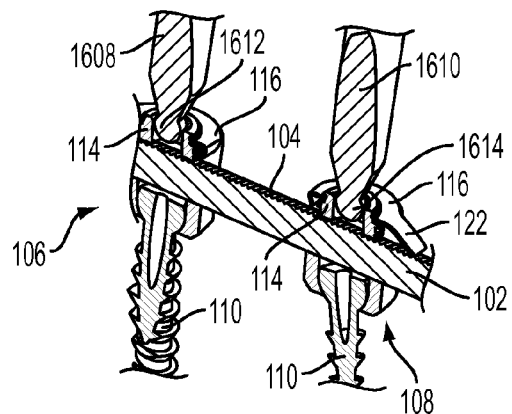
FIG. 50 illustrates a sectional view of the compressor tool shown in FIG. 49 engaging the two adjacent bone screws.

FIG. 50 illustrates a detailed sectional view of the compressor tool 1600 shown in FIG. 49 engaging the two adjacent bone screws 106, 108 of a screw-rod construct. The screw-rod construct shown includes toothed rod 102 with ratchet teeth 104, and first and second bone screws 106, 108 attached thereto. In FIG. 50, as in the illustrated example of FIG. 2, each bone screw 106, 108 includes a threaded shaft 110, a screw head 112, a set screw 114, and a pawl 116. The first and second angled extension portions 1610, 1608 may include respective distal ball tips 1614, 1612 which are configured to be received in set screws 114 for manipulation of the bone screws 106, 108 along the toothed rod 102. By using the compressor tool 1600 (or 1700), a surgeon can ratchet adjacent bone screws 106, 108 (and, hence, respective vertebrae) toward each other along the toothed rod 102 until a desired position and/or force is reached, at which point the surgeon can tighten the set screws 114 to rigidly secure the bone screws 106, 108 to the toothed rod 102. Likewise, the modified compressor tool 1700 shown in FIG. 51 can include tips 1712, 1714 and can be similarly utilized.

Figure 52:
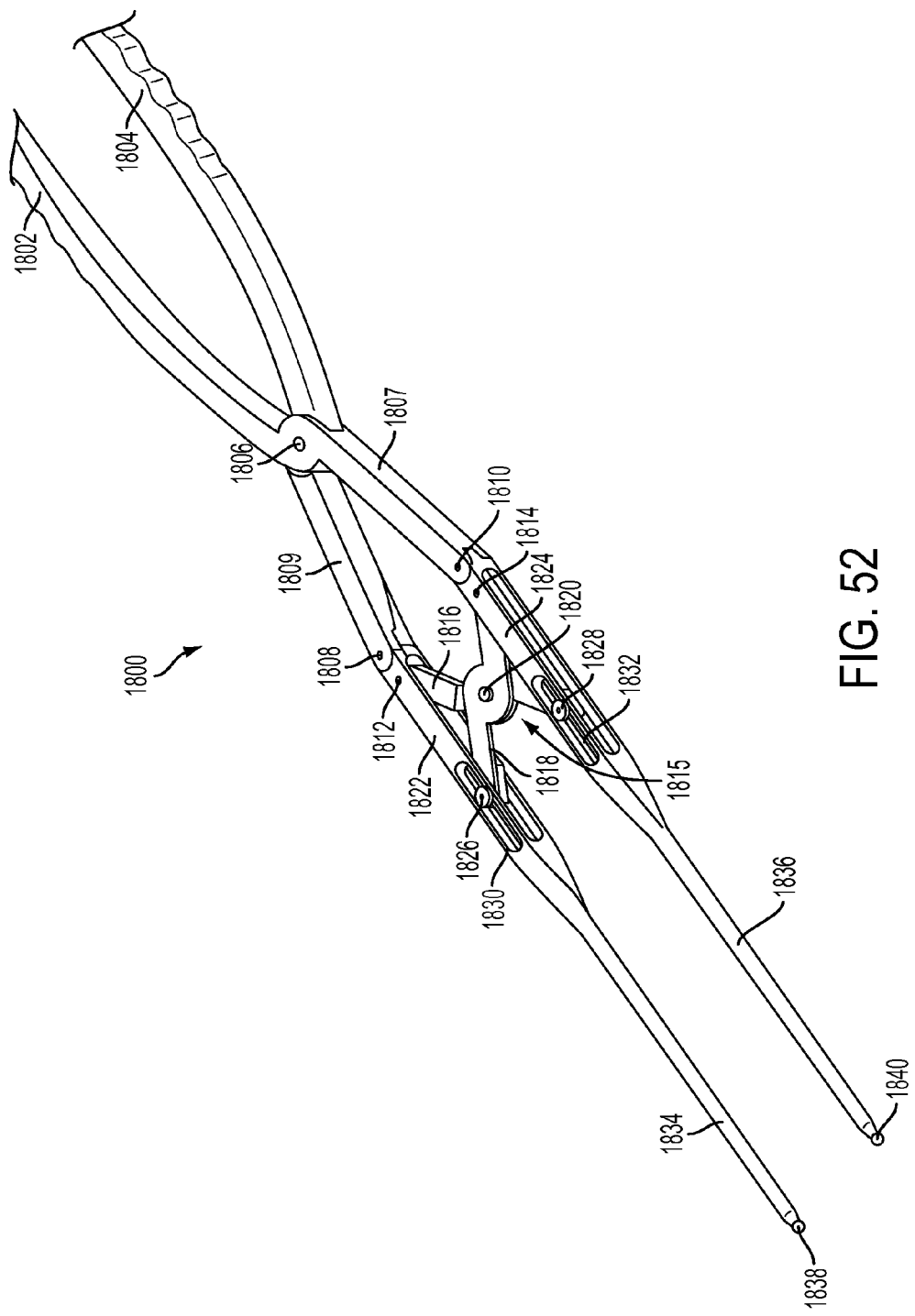
FIG. 52 illustrates a perspective view of a compressor tool according to yet another embodiment of the present technology.

FIG. 52 illustrates a perspective view of a compressor tool 1800 according to yet another embodiment, which is configured to engage and compress adjacent bone screws in a substantially linear fashion, and which may be utilized with any of the above-described ratcheting screw-rod constructs. The compressor tool 1800 may include first and second handle portions 1802, 1804 which may be ergonomically formed for gripping by a surgeon. In the manner of a pair of pliers, the first and second handle portions 1802, 1804 may be pivotably coupled to one another at a common fulcrum or pivot pin 1806. The first handle portion 1802 may be connected to a first extension portion 1807 and the second handle portion 1804 may be connected to a second extension portion 1809. The first and second extension portions 1807, 1809 may each be pivotably coupled at an end thereof to respective further first and second extension portions 1824, 1822 by pivot pins 1810, 1808, respectively. The further first and second extension portions 1824, 1822, are additionally coupled to one another via a secondary scissor mechanism 1815. Secondary scissor mechanism 1815 includes first and second crossing levers 1816, 1818 pivotably coupled to each other at a central fulcrum 1820. A first end of first crossing lever 1816 is pivotably coupled to the second extension portion 1822 by a pivot pin 1812 at a position proximate the pivot pin 1808. A first end of second crossing lever 1818 is pivotably coupled to the first extension portion 1824 by a pivot pin 1814 at a position proximate the pivot pin 1810. A second end of the first crossing lever 1816 includes a journal 1828 slidably and pivotably received within a longitudinally extending slot 1832 in the further first extension portion 1824. Likewise, a second end of the second crossing lever 1818 includes a journal 1826 slidably and pivotably received within a longitudinally extending slot 1830 in the further second extension portion 1822. The further first and second extension portions 1824, 1822 also include tip extensions 1836, 1834, respectively, which in turn include respective ball tips 1840, 1838 configured to engage the set screws of adjacent bone screws to be manipulated. As noted above, the foregoing structure of compressor tool 1800 allows a surgeon gripping the device to squeeze handles 1802, 1804 and thereby move ball tips 1840, 1838 substantially linearly toward (or away from) one another while maintaining tip extensions 1836, 1834 substantially parallel to one another. The parallel compressor tool 1800 may fit down two parallel tubes for minimally invasive spine (MIS) techniques.

Figure 53:
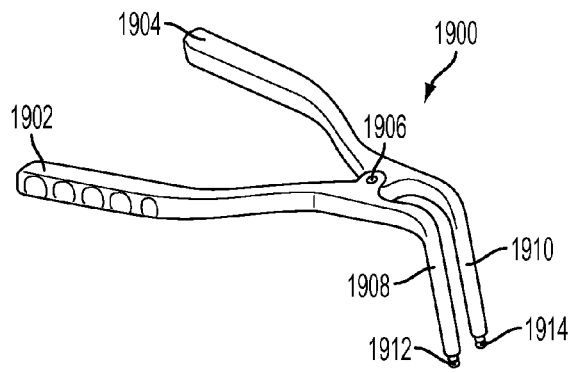
FIG. 53 illustrates a perspective view of a distractor tool according to an embodiment of the present technology, which tool is configured to engage and manipulate two adjacent bone screws.
Figure 54:
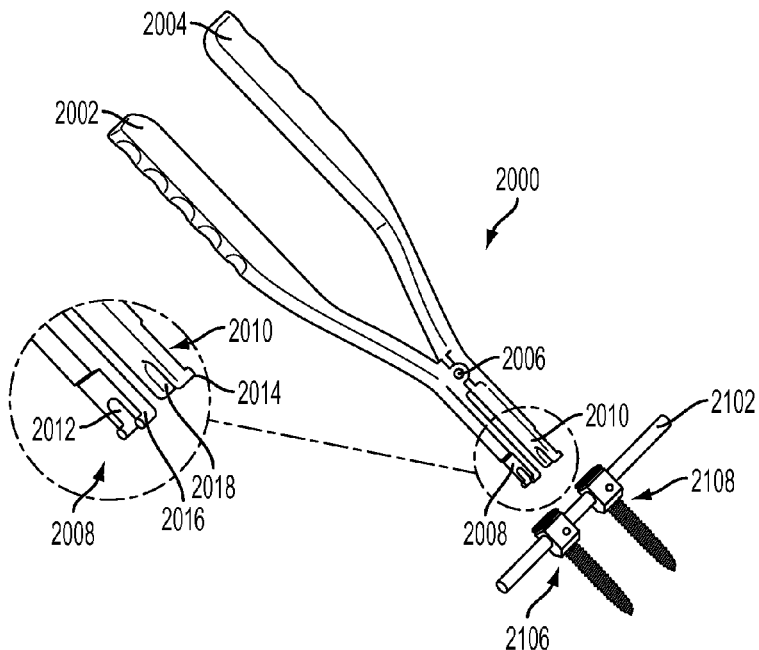
FIG. 54 illustrates a perspective view of a distractor tool according to another embodiment of the present technology, which tool is shown engaging and manipulating two adjacent bone screws.
Figure 55:
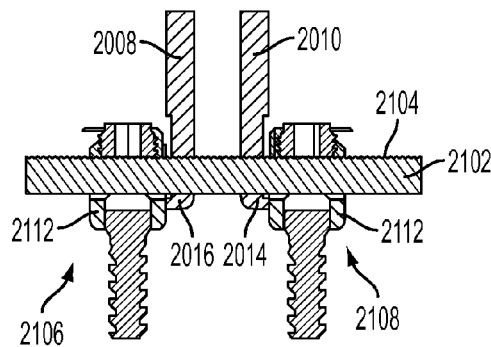
FIG. 55 illustrates a sectional view of the distractor tool shown in FIG. 54 engaging the two adjacent bone screws.

FIGS. 53 through 55 depict example embodiments of some distractor (retractor) tools according to several embodiments of the invention, each of which are configured to engage and separate adjacent bone screws, and which may be utilized with any of the above-described ratcheting screw-rod constructs. FIG. 53, for example, illustrates a perspective view of a distractor tool 1900 configured to engage and manipulate two adjacent bone screws (not shown in FIG. 53) according to an embodiment. The distractor tool 1900 may include first and second handle portions 1902, 1904 which may be ergonomically formed for gripping by a surgeon. The first and second handle portions 1902, 1904 may be pivotably coupled to one another a pivot point 1906. Unlike the compressor tools described above, however, the handle portions 1902, 1904 do not cross over one another at such pivot point 1906. Rather, here the first handle portion 1902 may be connected to a first angled extension portion 1908 and the second handle portion 1904 may be connected to a second angled extension portion 1910. The first and second angled extension portions 1908, 1910 may extend at an angle relative to a plane defined by the first and second handle portions 1902, 1904 such as, for example, in a direction substantially parallel to an axis of the pivot point 1906, although other angles (not shown) are also possible. The first and second angled extension portions 1908, 1910 may include respective ball tips 1912, 1914 which are configured to be received in set screws for manipulation of adjacent bone screws along a toothed rod. By using the distractor tool 1900, a surgeon can ratchet adjacent bone screws (and, hence, respective vertebrae) away from each other along the toothed rod until a desired position and/or force is reached, at which point the surgeon can tighten the set screws to rigidly secure the bone screws to the toothed rod.

FIG. 54 illustrates a perspective view of a distractor tool 2000 according to another embodiment. The distractor tool 2000 is shown engaging and manipulating two adjacent bone screws 2106, 2108 moveably coupled to a toothed rod 2102 having ratchet teeth 2104. FIG. 55 illustrates a sectional view of the distractor tool 2000 shown in FIG. 54 engaging the two adjacent bone screws 2106, 2108. The distractor tool 2000 may include first and second handle portions 2002, 2004 which may be ergonomically formed for gripping by a surgeon. The first and second handle portions 2002, 2004 may be pivotably coupled to one another a pivot point 2006. Unlike the compressor tools described above, however, the handle portions 2002, 2004 do not cross over one another at such pivot point 2006. Rather, here the first handle portion 2002 may be connected to a first extension portion 2008 and the second handle portion 2004 may be connected to a second extension portion 2010. The first and second extension portions 2008, 2010 are shown extending in the same plane as the handle portions 2002, 2004, but may extend at an angle relative to a plane defined by the first and second handle portions 2002, 2004 such as, for example, in a direction substantially parallel to an axis of the pivot point 2006, although other angles (not shown) are also possible. The first and second extension portions 2008, 2010 may include respective distal tips each of which may include an open U-shaped recess 2012, 2014 configured to receive the toothed rod 2102 and contact a side of the respective screw heads 2112 of the bone screws 2106, 2108 for ratcheted manipulation of the bone screws 2106, 2108 away from one another along the toothed rod 2102. The extension portions 2008, 2010 may also include multiple protrusions 2016, 2018, respectively, for positively engaging the sides of the bone screws 2106, 2108. That is, by using the distractor tool 2000, a surgeon can ratchet the adjacent bone screws 2106, 2108 (and, hence, respective vertebrae) away from each other along the toothed rod 2102 until a desired position and/or force is reached, at which point the surgeon can tighten the set screws to rigidly secure the bone screws 2106, 2108 to the toothed rod 2102. A compressor tool (not shown) with similarly structured distal tips may also be provided which is constructed to engage outer sides of the adjacent bone screws 2106, 2108 and ratchet the same toward each other along the toothed rod 2102.

EXAMPLE

A screw-rod construct of the present technology was made in accordance with the example illustrated in FIGS. 2-6. The toothed rod had triangular ratchet teeth formed by cutting grooves having a 90° angle along the length of the toothed rod. The grooves were cut about 0.75 mm apart, and were cut radially in an arc that was about 60°. The toothed rod had an inner diameter of about 5.5 mm, and was made from Grade 23 Titanium alloy (Ti6Al4V-ELI). The pawl was also made of Grade 23 Titanium alloy (Ti6Al4V-ELI), and was about 0.016 inches (0.4 mm) thick. The blade of the pawl was about 5 mm wide.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

We claim:

1. A compression-distraction spinal fixation system comprising:
    a bone screw comprising a pawl; and
    a toothed rod having a plurality of ratchet teeth,
    wherein the pawl includes a blade portion arranged to engage the ratchet teeth on the toothed rod when the pawl is in a first position,
    wherein the bone screw is releasably coupled to the toothed rod and selectively moveable in a movement direction having a movement axis along the toothed rod,
    wherein the blade portion extends from the bone screw in a direction along the movement axis and engages the ratchet teeth of the toothed rod to allow unidirectional movement of the bone screw in the movement direction along the toothed rod, and
    wherein the pawl is rotatable from the first position relative to the toothed rod to disengage the pawl from the ratchet teeth on the toothed rod,
    wherein the pawl is rotatable approximately 180° from the first position to a second position, to engage the blade portion with the ratchet teeth on the toothed rod.

2. The compression-distraction spinal fixation system of claim 1, wherein the pawl is rotatably connected to the bone screw.

3. The compression-distraction spinal fixation system of claim 2, wherein the pawl is selectively rotatable about the bone screw between the first position and the second position.

4. The compression-distraction spinal fixation system of claim 1, wherein the bone screw further comprises a set screw, and the pawl is rotatably coupled to the set screw.

5. The compression-distraction spinal fixation system of claim 4, wherein the pawl is retained on the set screw by a retaining ring.

6. The compression-distraction spinal fixation system of claim 4, wherein the blade portion extends substantially parallel to an axis of the set screw.

7. The compression-distraction spinal fixation system of claim 4, wherein the blade portion extends away from the set screw at an angle.

8. The compression-distraction spinal fixation system of claim 4, wherein the blade portion extends toward the set screw at an angle.

9. The compression-distraction spinal fixation system of claim 4, wherein the pawl covers a top surface of a screw head of the bone screw.

10. The compression-distraction spinal fixation system of claim 9, wherein an edge of the top surface of the screw head is chamfered and the pawl includes an angled surface configured to engage the chamfered edge.

11. The compression-distraction spinal fixation system of claim 10, wherein the pawl includes a detent in the angled surface arranged to engage a non-threaded portion of the screw head to selectively prevent rotation of the pawl relative to the screw head.

12. The compression-distraction spinal fixation system of claim 10, further comprising the blade portion extending from the angled surface of the pawl and configured to engage the ratchet teeth on the toothed rod.

13. The compression-distraction spinal fixation system of claim 1, further comprising a second bone screw comprising a pawl, wherein the second bone screw is releasably coupled to and selectively moveable along the toothed rod, and wherein the pawl of the second bone screw engages the ratchet teeth of the toothed rod, whereby the first and second bone screws are selectively moveable toward or away from one another to alter a distance therebetween.

14. The compression-distraction spinal fixation system of claim 1, wherein the blade portion that engages the ratchet teeth in the first position is the same blade portion that engages the ratchet teeth in the second position.

15. A spinal fixation kit, comprising:
    a bone screw comprising a pawl;
    a toothed rod having a plurality of ratchet teeth,
    wherein the pawl includes a blade portion arranged to engage the ratchet teeth on the toothed rod,
    wherein the bone screw is configured to be releasably coupled to and selectively moveable along a movement axis along the toothed rod,
    wherein the blade portion extends from the bone screw in a direction along the movement axis and is configured to engage the ratchet teeth of the toothed rod to allow unidirectional movement of the bone screw in a first movement direction along the toothed rod,
    wherein the pawl is rotatable approximately 180° relative to the toothed rod and configured to engage the ratchet teeth of the toothed rod to allow unidirectional movement of the bone screw in a second movement direction along the toothed rod; and
    a compression tool including:
        first and second handle portions pivotably coupled to one another about a common fulcrum; and
        first and second extension portions connected, respectively, to the first and second handle portions and including distal tips configured to engage a portion of the bone screw to allow manual manipulation of the bone screw unidirectionally along a toothed rod of the spinal fixation system.

16. A spinal fixation kit, comprising:
    a bone screw comprising a pawl;
    a toothed rod having a plurality of ratchet teeth,
    wherein the pawl includes a blade portion arranged to engage the ratchet teeth on the toothed rod,
    wherein the bone screw is configured to be releasably coupled to and selectively moveable in a movement direction having a movement axis along the toothed rod, wherein the blade portion extends from the bone screw in a direction along the movement axis and is configured to engage the ratchet teeth of the toothed rod to allow unidirectional movement of the bone screw along the toothed rod, and wherein the pawl is rotatable approximately 180° relative to the toothed rod and configured to engage the ratchet teeth of the toothed rod to allow unidirectional movement of the bone screw in a second movement direction along the toothed rod; and a distraction tool including:
   first and second handle portions pivotably coupled to one another at a pivot point; and
   first and second extension portions connected, respectively, to the first and second handle portions and including distal tips configured to engage a portion of the bone screw to allow manual manipulation of the bone screw unidirectionally along a toothed rod of the spinal fixation system.

* * * * *